United States Patent
Voute et al.

(10) Patent No.: US 7,104,074 B2
(45) Date of Patent: Sep. 12, 2006

(54) SYSTEMS AND METHODS FOR FREEZING, STORING, TRANSPORTING AND THAWING BIOPHARMACEUTICAL MATERIAL

(75) Inventors: Nicolas Voute, Cuges les Pins (FR); Eric K. Lee, Acton, MA (US); James Edward DeBeers, Chicago, IL (US); Brian J. Woodward, Chicago, IL (US); Ngee Jenn Lee, Norridge, IL (US)

(73) Assignee: Integrated Biosystems, Inc., Napa, CA (US)

( * ) Notice: Subject to any disclaimer, the term of this patent is extended or adjusted under 35 U.S.C. 154(b) by 93 days.

(21) Appl. No.: 10/455,223

(22) Filed: Jun. 4, 2003

(65) Prior Publication Data

US 2005/0011202 A1    Jan. 20, 2005

Related U.S. Application Data

(63) Continuation-in-part of application No. 10/254,036, filed on Sep. 23, 2002, now Pat. No. 6,698,213, and a continuation-in-part of application No. 10/254,025, filed on Sep. 23, 2002, now Pat. No. 6,684,646.

(60) Provisional application No. 60/334,622, filed on Nov. 1, 2001, provisional application No. 60/334,622, filed on Nov. 1, 2001.

(51) Int. Cl.
   *F25D 15/00*    (2006.01)
(52) U.S. Cl. .............................. 62/62; 62/237; 280/79.3
(58) Field of Classification Search .................. 62/237, 62/291, 62; 280/79.3, 79.11
   See application file for complete search history.

(56) References Cited

U.S. PATENT DOCUMENTS

| 2,068,401 | A | * | 1/1937 | Dromgold | 62/291 |
| 2,506,448 | A | * | 5/1950 | Gregor | 62/159 |
| 2,662,520 | A | | 12/1953 | McMahon | 128/1 |
| 2,775,101 | A | | 12/1956 | Hanson | 62/108 |
| 2,964,920 | A | | 12/1960 | Staebler | 62/60 |
| 2,966,041 | A | | 12/1960 | Zearfoss, Jr. et al. | 62/60 |

(Continued)

FOREIGN PATENT DOCUMENTS

DE         3047784 A1    7/1982

(Continued)

OTHER PUBLICATIONS

Stahl, A.L., "Concentration of Citruc Juices by Freezing", Florida State Horticultural Society, 1944, pp. 43-45.

(Continued)

*Primary Examiner*—William E. Tapolcai
(74) *Attorney, Agent, or Firm*—Heslin Rothenberg Farley & Mesiti P.C.; Nicholas Mesiti, Esq.; Victor A. Cardona, Esq.

(57) ABSTRACT

A system for freezing, thawing, transporting, and storing a biopharmaceutical material, which includes a container, a supporting structure, a temperature control unit, and a transportation cart. The container is adapted to receive the biopharmaceutical material therein for freezing, thawing, storing, and transporting, with the container also being receivable in the supporting structure. The temperature control unit has a cavity for receiving the supporting structure, when the supporting structure supports the container, and the transportation cart has a channel for receiving the supporting structure, when the supporting structure supports the container.

24 Claims, 19 Drawing Sheets

U.S. PATENT DOCUMENTS

| | | | | |
|---|---|---|---|---|
| 3,121,627 A | | 2/1964 | Harris | 62/58 |
| 3,389,974 A | | 6/1968 | Barattini et al. | 23/295 |
| 3,690,118 A | * | 9/1972 | Rainwater | 62/250 |
| 3,940,232 A | | 2/1976 | Stock | 425/447 |
| 3,952,536 A | | 4/1976 | Faust et al. | 62/293 |
| 3,959,971 A | | 6/1976 | Anderson | 62/135 |
| 4,018,911 A | | 4/1977 | Lionetti et al. | 424/101 |
| 4,030,314 A | | 6/1977 | Strehler et al. | 62/65 |
| 4,077,228 A | * | 3/1978 | Schumacher et al. | 62/256 |
| 4,090,374 A | | 5/1978 | Faust et al. | 62/341 |
| 4,107,937 A | | 8/1978 | Chmiel | 62/64 |
| 4,178,776 A | | 12/1979 | Baldus et al. | 62/538 |
| 4,194,369 A | | 3/1980 | Faust et al. | 62/371 |
| 4,251,995 A | | 2/1981 | Pert et al. | 62/60 |
| 4,304,293 A | | 12/1981 | Scheiwe et al. | 165/12 |
| 4,327,799 A | | 5/1982 | Scheiwe et al. | 165/2 |
| 4,336,435 A | | 6/1982 | Kashyap et al. | 219/10.55 |
| 4,469,227 A | | 9/1984 | Faust | 206/527 |
| 4,473,739 A | | 9/1984 | Scheiwe et al. | 219/302 |
| 4,484,448 A | * | 11/1984 | Crabb, Jr. | 62/64 |
| 4,486,389 A | | 12/1984 | Darnell et al. | 422/307 |
| 4,490,982 A | | 1/1985 | Christmas | 62/3 |
| 4,531,373 A | | 7/1985 | Rubinsky | 62/63 |
| 4,565,073 A | | 1/1986 | Lavender | 62/373 |
| 4,580,409 A | | 4/1986 | Angelier et al. | 62/340 |
| 4,584,843 A | | 4/1986 | Pronger, Jr. et al. | 62/123 |
| 4,587,810 A | | 5/1986 | Fletcher | 62/3 |
| 4,596,120 A | | 6/1986 | Knodel et al. | 62/59 |
| 4,609,036 A | | 9/1986 | Schrader | 165/10 |
| 4,652,712 A | | 3/1987 | Zeipel | 219/10.55 |
| 4,669,271 A | | 6/1987 | Noel | 62/60 |
| 4,712,607 A | | 12/1987 | Lindeman et al. | 165/30 |
| 4,720,048 A | * | 1/1988 | Maroney et al. | 280/47.34 |
| 4,793,151 A | | 12/1988 | Masel et al. | 62/306 |
| 4,799,358 A | | 1/1989 | Knopf et al. | 62/3 |
| 4,801,777 A | | 1/1989 | Auerbach | 219/10.55 |
| 4,843,827 A | | 7/1989 | Peppers | 62/73 |
| 4,852,365 A | * | 8/1989 | Elrod et al. | 62/237 |
| 4,874,915 A | | 10/1989 | Harms et al. | 219/10.55 |
| 4,893,670 A | | 1/1990 | Joshi et al. | 165/40 |
| 4,922,721 A | * | 5/1990 | Robertson et al. | 62/3.61 |
| 4,954,679 A | | 9/1990 | Harms et al. | 219/10.55 |
| 4,967,564 A | | 11/1990 | Strasser | 62/47.1 |
| 4,971,737 A | | 11/1990 | Infanti | 264/28 |
| 4,976,308 A | | 12/1990 | Faghri | 165/10 |
| 4,986,080 A | | 1/1991 | Grigoli et al. | 62/75 |
| 5,005,371 A | | 4/1991 | Yonezawa et al. | 62/238.6 |
| 5,022,149 A | | 6/1991 | Abbott | 29/890.048 |
| 5,022,235 A | | 6/1991 | Grissom | 62/529 |
| 5,029,634 A | | 7/1991 | Hurner | 165/47 |
| 5,033,544 A | | 7/1991 | Abbott | 165/184 |
| 5,054,548 A | | 10/1991 | Zohler | 165/133 |
| 5,072,569 A | | 12/1991 | VanTassel | 52/745 |
| 5,090,207 A | | 2/1992 | Gilbertson et al. | 62/529 |
| 5,103,651 A | | 4/1992 | Coelho et al. | 62/341 |
| 5,125,900 A | | 6/1992 | Teves | 604/114 |
| 5,168,725 A | | 12/1992 | Margolin | 62/457.9 |
| 5,176,197 A | | 1/1993 | Hamaguchi et al. | 164/459 |
| 5,181,387 A | | 1/1993 | Meckler | 62/59 |
| 5,205,128 A | | 4/1993 | Richard | 62/63 |
| 5,212,957 A | | 5/1993 | Ruff | 62/124 |
| 5,220,954 A | | 6/1993 | Longardner et al. | 165/10 |
| 5,243,833 A | | 9/1993 | Coelho et al. | 62/376 |
| 5,285,657 A | | 2/1994 | Bacchi et al. | 62/457.9 |
| 5,332,034 A | | 7/1994 | Chiang et al. | 165/184 |
| 5,374,436 A | | 12/1994 | White et al. | 426/249 |
| 5,411,078 A | | 5/1995 | Ares | 165/113 |
| 5,458,191 A | | 10/1995 | Chiang et al. | 165/133 |
| 5,476,763 A | | 12/1995 | Bacchi et al. | 435/284.1 |
| 5,520,885 A | | 5/1996 | Coelho et al. | 422/101 |
| 5,524,706 A | | 6/1996 | Nakamura et al. | 165/47 |
| 5,535,598 A | | 7/1996 | Cothern et al. | 62/356 |
| 5,557,943 A | | 9/1996 | Coelho et al. | 62/376 |
| 5,579,830 A | | 12/1996 | Giammaruti | 165/104.27 |
| 5,582,856 A | | 12/1996 | White et al. | 426/249 |
| 5,609,035 A | * | 3/1997 | Cothern et al. | 62/73 |
| 5,616,268 A | | 4/1997 | Carr | 219/687 |
| 5,626,353 A | * | 5/1997 | Campbell | 280/47.35 |
| 5,638,686 A | | 6/1997 | Coelho et al. | 62/51.1 |
| 5,644,922 A | | 7/1997 | Linden et al. | 62/51.1 |
| 5,689,961 A | | 11/1997 | Cosman | 62/78 |
| 5,750,658 A | | 5/1998 | Coelho et al. | 530/382 |
| 5,779,974 A | | 7/1998 | Kuzyk | 422/44 |
| 5,862,675 A | | 1/1999 | Scaringe et al. | 62/193.3 |
| 5,863,715 A | | 1/1999 | Rajotte et al. | 435/1.3 |
| 5,873,254 A | | 2/1999 | Arav | 62/63 |
| 5,884,490 A | | 3/1999 | Whidden | 62/70 |
| 5,939,023 A | | 8/1999 | Coelho et al. | 422/101 |
| 5,964,007 A | | 10/1999 | Wisniewski | 62/373 |
| 5,964,095 A | | 10/1999 | Coelho et al. | 62/62 |
| 5,988,422 A | | 11/1999 | Vallot | 220/62.22 |
| 5,996,427 A | | 12/1999 | Masek et al. | 73/864.91 |
| 5,999,701 A | | 12/1999 | Schmidt | 392/470 |
| 6,007,773 A | | 12/1999 | Kuzyk | 422/44 |
| 6,065,294 A | | 5/2000 | Hammerstedt et al. | 62/3.3 |
| 6,077,447 A | | 6/2000 | Coelho et al. | 210/774 |
| 6,079,215 A | | 6/2000 | Wisniewski | 62/46.1 |
| 6,098,410 A | | 8/2000 | Horigane | 62/62 |
| 6,123,696 A | | 9/2000 | Coelho et al. | 604/410 |
| 6,146,124 A | | 11/2000 | Coelho et al. | 425/387.1 |
| 6,155,071 A | * | 12/2000 | Koyanagi | 62/457.2 |
| 6,186,468 B1 | * | 2/2001 | Schlegel | 248/678 |
| 6,196,296 B1 | | 3/2001 | Wisniewski et al. | 165/47 |
| 6,218,796 B1 | * | 4/2001 | Kozlowski | 318/280 |
| 6,220,038 B1 | | 4/2001 | Marsh et al. | 62/71 |
| 6,232,115 B1 | | 5/2001 | Coelho et al. | 435/307.1 |
| 6,274,090 B1 | | 8/2001 | Coelho et al. | 422/101 |
| 6,302,327 B1 | | 10/2001 | Coelho et al. | 235/383 |
| 6,347,526 B1 | * | 2/2002 | Ledbetter | 62/237 |
| 6,371,121 B1 | | 4/2002 | Faries, Jr. et al. | 128/849 |
| 6,384,380 B1 | | 5/2002 | Faries, Jr. et al. | 219/385 |
| 6,387,322 B1 | | 5/2002 | Gallus | 422/38 |
| 6,393,860 B1 | | 5/2002 | Heschel et al. | 62/376 |
| 6,453,683 B1 | | 9/2002 | Wisniewski et al. | 62/75 |
| 6,773,081 B1 | * | 8/2004 | Yuyama et al. | 312/321 |

FOREIGN PATENT DOCUMENTS

| | | |
|---|---|---|
| DE | 3833753 A1 | 8/1989 |
| DE | 4029216 | 3/1992 |
| EP | 0195919 A2 | 2/1986 |
| EP | 0318924 | 6/1989 |
| EP | 0647707 A2 | 7/1994 |
| EP | 0726080 A2 | 12/1995 |
| EP | 1 134 000 A2 | 9/2001 |
| FR | 758510 | 1/1934 |
| FR | 2501057 | 10/1981 |
| GB | 2 196 830 A | 5/1988 |
| GB | 2240165 A | 7/1991 |
| GB | 2351799 A | 1/2001 |
| WO | WO 97/18424 | 5/1997 |
| WO | WO 97/24152 | 7/1997 |
| WO | WO 98/23907 | 6/1998 |
| WO | WO 98/34078 | 8/1998 |
| WO | WO 00/72902 | 12/2000 |

OTHER PUBLICATIONS

Kalhori, B. et al., "Studies on Heat Transfer From a Vertical Cylinder, With or Without Fins, Embedded in a Solid Phse Change Mediam", Transactions of the ASME, Journal of Heat Transfer, vol. 107, Feb. 1985, pp. 44-51.

Wisniewski, et al., "Large-Scale Freezing and Thawing of Biopharmaceutical Drug Product", Proceedings of the International Congress: Advanced Technologies for Manufacturing of Aseptic &

Terminally Sterilized Pharmaceuticals & Biopharmaceuticals, Basel, Switzerland, Feb. 17-19, 1992, pp. 132-140.

Wisniewski et al., Large-Scale Freezing and Thawing of Biopharmaceutical Drug Product, PharmTech Conference, Sept. 16-19, 1996, Sheraton Meadowlands, East Rutherford, New Jersey.

Wisniewski, et al., "Large-Scale Freezing and Thawing of Biopharmaceutical Products", Biotechnology and Biopharmaceutical Manufacturing, Processing and Preservation, pp. 7-59.

Wisniewski, Richard, "Developing Large-Scale Cryopreservation Systems for Biopharmaceutical Products", BioPharm, Jun. 1998, pp. 50-60.

Wu, et al., "Scale-Down Approach to Large Volume Cryopreservation of Biopharmaceuticals Using the CryoCassette ™ and CryoWedge ™", Integrated Biosystems, 2000, 4 pages.

L. Quan et al., "Effects of Vibration on Ice Contact Melting Within Rectangular Enclosures", Transactions of the ASME 120:518-520 (May 1998).

Burton et al., "An Experimental Investigation of the Solidification Process in a V-Shaped Sump", Inter. J. Heat Mass Transfer, vol. 18, pp. 2383-2393, 1995.

Avis et al., *CRYOPRESERVATION Applications in Pharmaceuticals and Biotechnology*, Drug Manufacturing Technology Series 5, "Large-Scale Cryopreservation: Process Development for Freezing and Thawing of Large Volumes of Cell Suspensions, Protein Solutions, and Biological Products", Wisniewski, pp. 181-197.

Wisniewski, Bioprocessing, Controlled Freeze/Thaw for Biopharmaceuticals, Tutorial: Preservation of Bioproducts Using Controlled Freeze/Thaw Operations, Genetic Engineering News, Feb. 15, 2003, vol. 32, No. 4, pp. 36 & 38.

Double Contact PlateFreezers, Dole Plate Freezers, www.bmil.com/dole, copyright 1996, BMIL International.

* cited by examiner

US 7,104,074 B2

SYSTEMS AND METHODS FOR FREEZING, STORING, TRANSPORTING AND THAWING BIOPHARMACEUTICAL MATERIAL

CROSS-REFERENCE TO RELATED APPLICATIONS

This application is a Continuation in part of U.S. application Ser. No. 10/254,036, filed on Sep. 23, 2002 now U.S. Pat. No. 6,698,213 and titled "Systems and Methods for Freezing, Storing and Thawing Biopharmaceutical Material", which claims the benefits of U.S. Provisional Application No. 60/334,622, filed Nov. 1, 2001, both of which are incorporated herein by reference Also, this application is a Continuation in part of U.S. application Ser. No. 10/254,025 filed on Sep. 23, 2002 and titled "Systems and Methods for Freezing, Storing, and Thawing Biopharmaceutical Material," which claims the benefit of U.S. Provisional Application No. 60/334,622, filed Nov. 1, 2001, both of which are incorporated herein by reference. Also, the contents of U.S. patent application Ser. No. 09/905,488, filed Jul. 13, 2001, entitled "Cryopreservation System with Controlled Dendritic Freezing Front Velocity" and U.S. patent application Ser. No. 09/863,126, entitled "Cryopreservation System with Controlled Dendritic Freezing Front Velocity", filed May 22, 2001, are incorporated herein by reference. This application also relates to U.S. patent application Ser. No. 10/455,222, filed on Jun. 4, 2003, and titled "Systems And Methods For Freezing, Storing And Thawing Biopharmaceutical Material," the contents of which are incorporated herein by reference.

TECHNICAL FIELD

This invention relates, in general, to biopharmaceutical materials, preservation methods and systems, and more particularly to systems and methods for transporting, freezing, storing, and thawing of biopharmaceutical materials.

BACKGROUND ART

Preservation of biopharmaceutical materials is important in the manufacture, use, transport, storage and sale of such materials. For example, biopharmaceutical materials are often preserved by freezing between processing steps and during storage. Similarly, biopharmaceutical materials are often frozen and thawed as part of the development process to enhance the quality or to simplify the development process.

When freezing biopharmaceutical materials, the overall quality, and in particular pharmaceutical activity, of the biopharmaceutical materials is desirably preserved, without substantial degradation of the biopharmaceutical materials.

Currently, preservation of biopharmaceutical material often involves placing a container containing liquid biopharmaceutical material in a cabinet freezer, chest freezer or walk-in freezer and allowing the biopharmaceutical material to freeze. Specifically, the container is often placed on a shelf in the cabinet freezer, chest freezer or walk-in freezer and the biopharmaceutical material is allowed to freeze. These containers may be stainless-steel vessels, plastic bottles or carboys, or plastic bags. They are typically filled with a specified volume to allow for freezing and expansion and then transferred into the freezers at temperatures typically ranging from negative 20 degrees Celsius to negative 70 degrees Celsius or below.

To ensure efficient use of available space inside the freezer, containers are placed alongside one another and sometimes are stacked into an array with varied spatial regularity. Under these conditions, cooling of the biopharmaceutical solution occurs at different rates depending on the exposure of each container to the surrounding cold air, and the extent to which that container is shielded by neighboring containers. For example, containers placed close to the cooling source or those on the outside of an array of containers would be cooled more rapidly than those further away from the cooling source and/or situated at the interior of the array.

In general, adjacent placement of multiple containers in a freezer creates thermal gradients from container to container. The freezing rate and product quality then depend on the actual freezer load, space between the containers, and air movement in the freezer. This results in a different thermal history for the contents of the containers depending on their location in a freezer, for example. Also, the use of different containers for individual portions of a single batch of biopharmaceutical material may cause different results for portions of the same batch due to different thermal histories resulting from freezing in a multiple container freezer, particularly if the storage arrangement is haphazard and random. Another consequence of obtaining a range of freezing times is that certain containers may freeze so slowly that the target solute can no longer be captured within the ice phase, but remains in a progressively smaller liquid phase. This phenomenon is referred to as cyroconcentration. In some cases such cyroconcentration could result in precipitation of the biopharmaceutical product, thus resulting in product loss.

Disposable containers such as plastic bags or other flexible containers often are damaged, leading to loss of the biopharmaceutical material. Particularly, the volumetric expansion of the biopharmaceutical materials during freezing could generate excessive pressure in an over filled bag or in a pocket of occluded liquid adjoining the bag material, possibly leading to rupture or damage to the integrity of the bag. Moreover, handling of such disposable containers, such as plastic bags, during freezing, thawing, or transportation of these containers often result in damage thereof, due, for example, to shock, abrasion, impact, or other mishandling events arising from operator errors or inadequate protection of the bags in use.

Similarly, thawing of biopharmaceutical materials typically involved removing them from a freezer and allowing them to thaw at room temperature. Such uncontrolled thawing can also lead to product loss. Generally, rapid thawing of biopharmaceutical materials results in less product loss than slower thawing. Further, it may also be desirable to control temperature of the biopharmaceutical materials during a thawing process since exposure of some biopharmaceutical materials to elevated temperatures may also lead to product loss. For example, it may be desirable to maintain a thawing biopharmaceutical material at about 0° C. when still in liquid and solid form during thawing thereof.

Further, it may be necessary or desirable to transport the biopharmaceutical materials between various locations to accomplish the freezing, storing, and thawing steps described. Such transport should protect the containers holding the materials from being damaged in transit and additionally may maintain the biopharmaceutical materials at a specified temperature for preservation thereof.

Thus, there is a need for systems and methods for freezing, storing, transporting, and thawing of biopharmaceutical materials that are controlled, do not result in loss of biopharmaceutical material, but instead create conditions conducive to preserving the biopharmaceutical material in a uniform, repeatable fashion in a protected environment.

SUMMARY OF THE INVENTION

The present invention provides, in a first aspect, a system for transporting and storing biopharmaceutical material which includes a supporting structure configured to support a container of biopharmaceutical material. A channel is configured to receive the supporting structure and the container of biopharmaceutical material. At least one supporting rail is configured to operatively support the container in the channel.

The present invention provides, in a second aspect, a system for freezing, storing, transporting, or thawing a biopharmaceutical material which includes a container of biopharmaceutical material, a temperature control unit, a frame, and a movable cart. The frame is configured to support the container of biopharmaceutical material. The temperature control unit has a slot configured to receive the frame supporting the container and the moveable cart has a channel configured to receive the frame supporting the container.

The present invention provides, in a third aspect, a method for transporting or storing a biopharmaceutical material. The method includes attaching a container of biopharmaceutical material to a supporting structure for supporting the container. Further included is locating the supporting structure on a supporting rail of a transportation cart.

The present invention provides, in a fourth aspect, a method for transporting or storing a biopharmaceutical material which includes moving a frame supporting a container holding biopharmaceutical material from a cavity of a temperature control unit and/or an interior of a transportation cart onto a plurality of stationary support rails to support the frame.

The present invention provides, in a fifth aspect, a system for storing a biopharmaceutical material which includes a plurality of stationary rails configured to support a frame for supporting a container for holding biopharmaceutical materials. The plurality of supporting rails is dimensioned to have a substantially same height as at least one of a cart support rail of a transportation cart and a support member of a temperature control unit.

The present invention provides, in a sixth aspect, a system for transporting and storing biopharmaceutical material which includes a movable platform having a grid configured to receive a frame for supporting a container of biopharmaceutical material.

The present invention provides, in a seventh aspect, a method for transporting or storing a biopharmaceutical material. The method includes providing a movable cart having a grid configured to receive at least one frame. Further included is engaging a frame supporting a container of biopharmaceutical material with the grid to support the frame on the movable cart.

BRIEF DESCRIPTION OF THE DRAWINGS

The subject matter which is regarded as the invention is particularly pointed out and distinctly claimed in the claims at the conclusion of the specification. The foregoing and other features, and advantages of the invention will be readily understood from the following detailed description of preferred embodiments taken in conjunction with the accompanying drawings in which:

DETAILED DESCRIPTION

Figure 1:
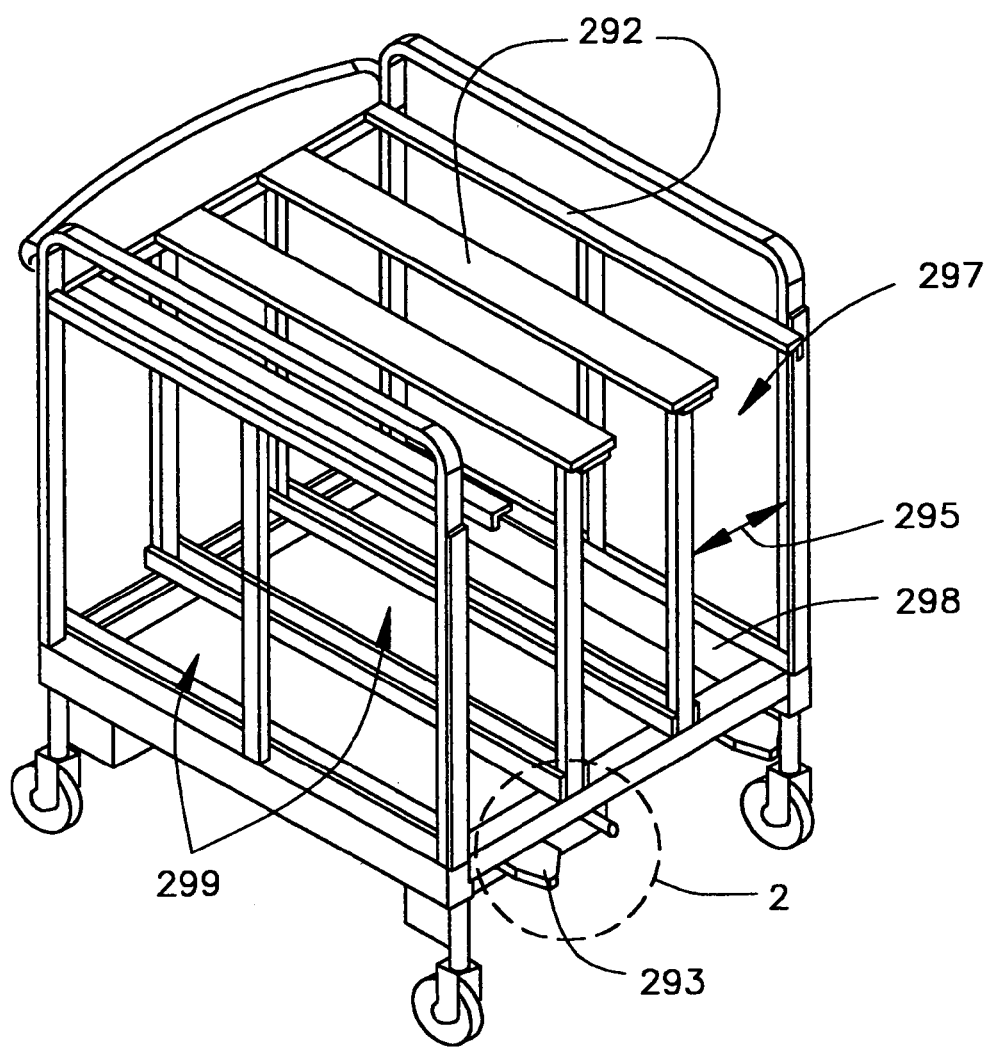
FIG. 1 is a perspective view of a transportation cart for transporting one or more frames and flexible containers, in accordance with the present invention.

In accordance with the principles of the present invention, systems and methods for freezing, storing, transporting and thawing biopharmaceutical material are provided.

In an exemplary embodiment depicted in FIGS. 1–8, portions of a system for cooling, freezing, preserving, processing, transporting, thawing, and storing biopharmaceutical material are shown. The system may include a transportation cart 290 configured to receive one or more sterile containers, such as flexible containers 10 adapted to contain the biopharmaceutical materials. Further, transportation cart 290 may include one or more cart channels 297 configured to receive one or more supporting structures, such as one or more frames 15, for supporting one or more containers 10.

Transportation cart 290 may be adapted to receive one or more frames 15, each for supporting a container 10 holding the biopharmaceutical material to allow the biopharmaceutical material to be transported and/or stored therein. For example, a width 230 (FIG. 8) of frame 15 may be less than or equal to a dimension or width 295 of a cart channel 297 of cart 290 to allow frame 15 to be received therein. Also, a bottom side 298 of cart channel 297 may be at a same or similar height as a bottom side 291 (FIGS. 3 and 7) of a control unit slot 25 of a temperature control unit 20 (e.g. a freeze-thaw module), as depicted in FIGS. 1 and 3 to allow frame 15 to be easily slid from cart 290 to slot 25 of temperature control unit 20, and vice versa.

Figure 3:
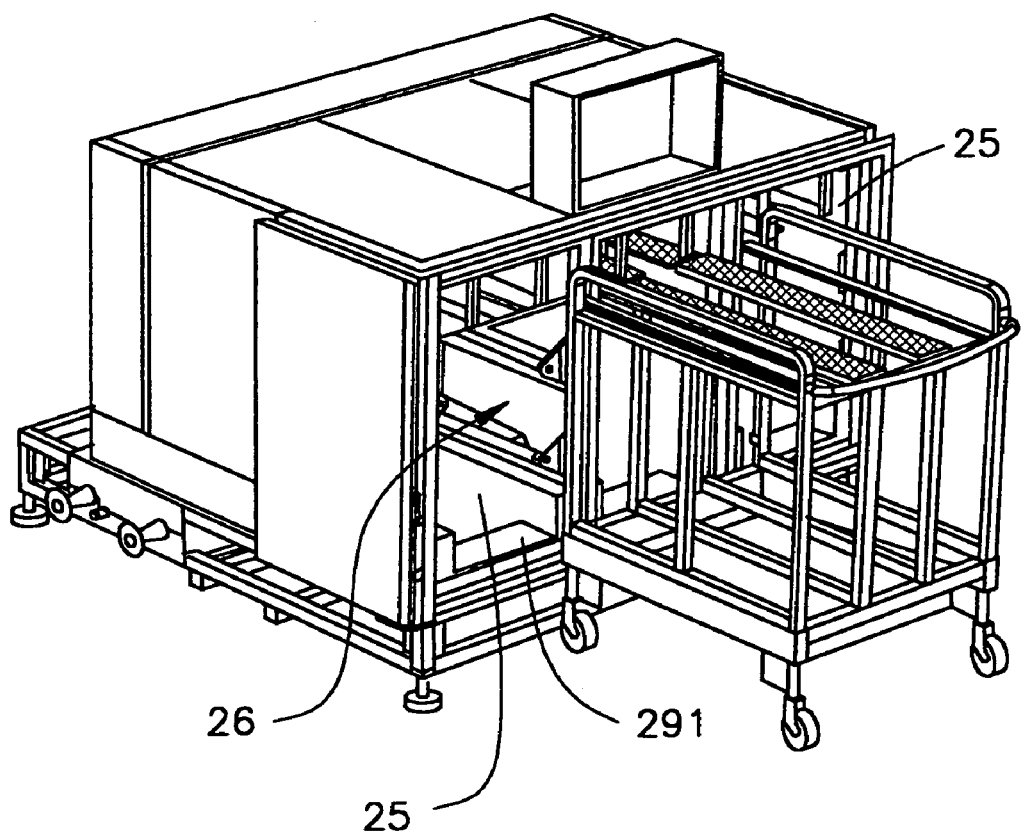
FIG. 3 is a perspective view of the cart of FIG. 1 adjacent to a temperature control unit for transporting a frame therebetween.
Figure 4:
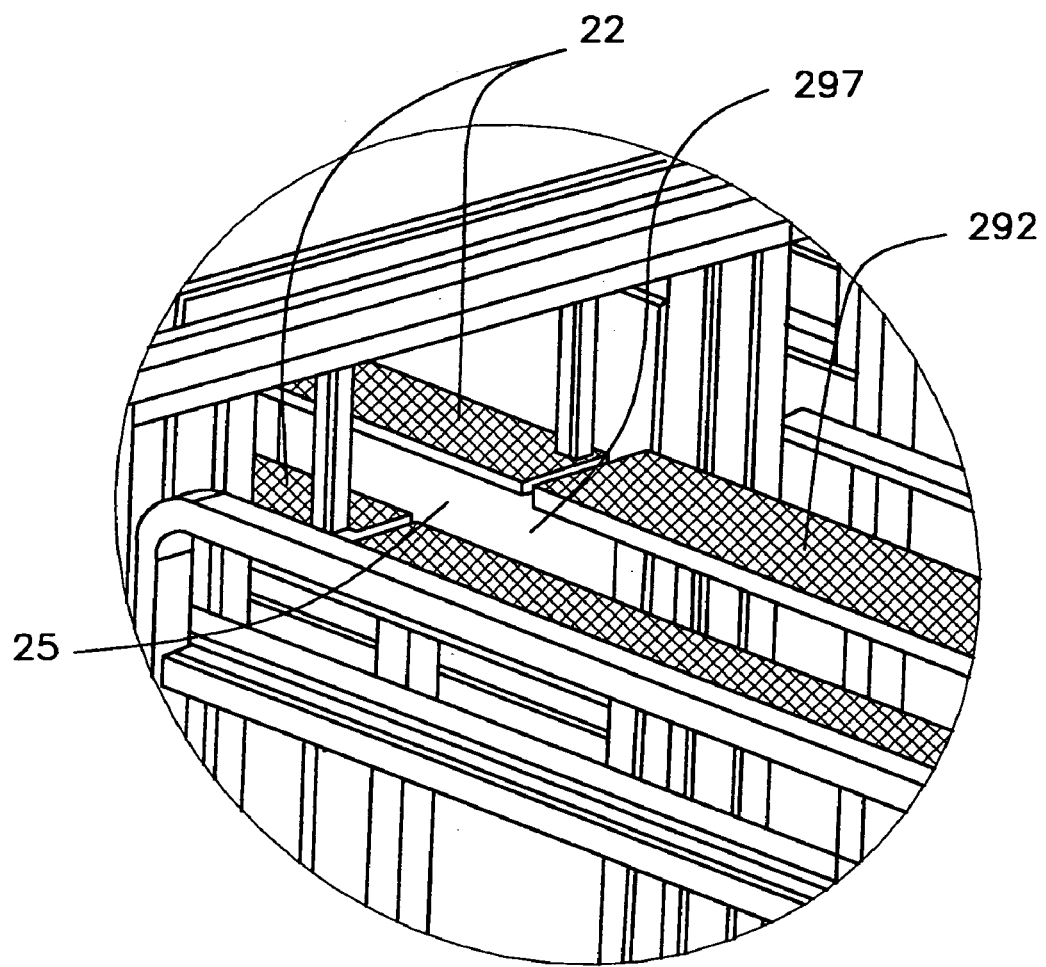
FIG. 4 is a perspective view of an enlarged portion of FIG. 3 particularly depicting the alignment of a support member of a temperature control unit and supporting rails of the transportation cart.

Temperature control unit 20 is configured to control the temperature of an interior 26 thereof which may include one or more slots 25, as depicted in FIGS. 3 and 4. Temperature control unit 20 may include a support member 22 for receiving frame 15 which may be slid off support member 22 into cart channel 297 of cart 290, for example.

Also, cart channel 297 may include one or more channel supports or support rails 292 for supporting frame 15 in cart channel 297. Cart 290 may include multiple cart channels 297 (e.g., three channels as depicted in FIG. 1) and support rails 292 to allow multiple frames holding respective multiple containers to be received therein for transport and/or storage. For example, cart 290 may include three channels 297 with each of channels 297 being configured to receive two 16.6 liters containers supported by frame 15 on rails 292. In such an arrangement cart 290 may receive six 16.6 liter containers resulting in a capacity of 100 liters. Alternatively, instead of each of channels 297 may receive four 8.3 liter containers, which thus results in cart 290 being configured to receive twelve 8.3 liter containers with a total capacity of 100 liters. Further, such support rails 292 and cart channels 297 may be located parallel to each other to maximize the number of frames and containers receivable in cart 290. In one example, a height of a top of support member 22 may be at a same height as a top of support rail 292 to facilitate movement of frame 15 therebetween. In a different example, a bottom of frame 15, when supported by support member 22, may be at a same height as a bottom 298 of cart channel 297 to facilitate movement of frame 15 into cart 290 and vice versa. Thus, frame 15 may be easily moved from slot 25 of interior 26 of temperature control unit 20 into channel 297 of cart by sliding frame 15 onto moveable support member 22 from cart 290 manually. For example, support rails 292 of cart 290 may be coated with or formed of a material allowing frame 15 to be easily slid by a user and support member 22 may be immobile.

Figure 2:
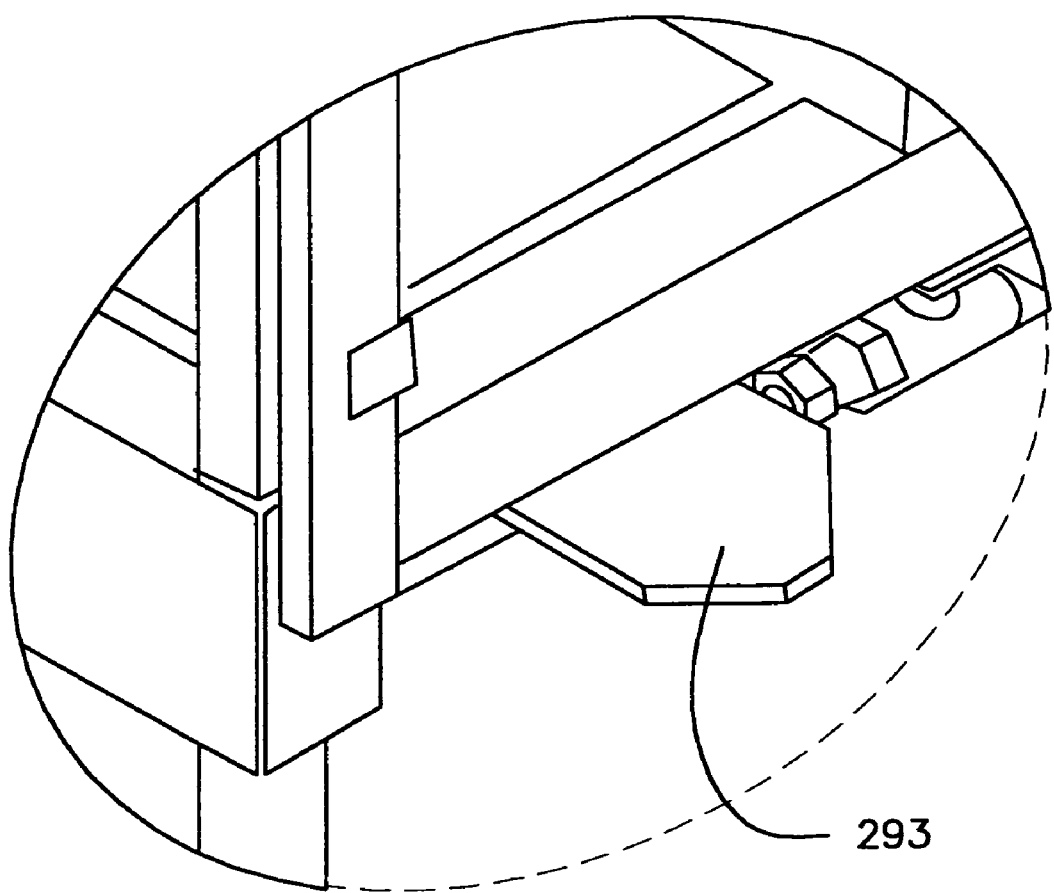
FIG. 2 is a perspective view of an enlarged portion of FIG. 1 particularly showing the alignment tabs thereof.

Cart 290 may also include one or more aligning or alignment tabs 293, as depicted in FIGS. 1 and 2. Alignment tabs 293 may be receivable in one or more receiving hollows or recesses (not shown) to align slot 25 with channel 297. Such alignment facilitates the sliding of frame 15 from cart 290 to slot 25 of interior 26 of temperature control unit 20 or vice versa. More specifically, as depicted in FIG. 4, support member 22 may be aligned with rails 292 such that frame 15 may be slid in a straight line from temperature control unit 20 to cart 290 or vice versa. Alternatively, in an example not shown, temperature control unit 20 could include aligning tabs (not shown) receivable in recesses (not shown) of cart 290. In a further example, temperature control unit 20 could include one or more recesses and one or more tabs while cart 290 may also include one or more recesses and one or more tabs with respective tabs being received in respective recesses to align the temperature control unit and cart.

Figure 5:
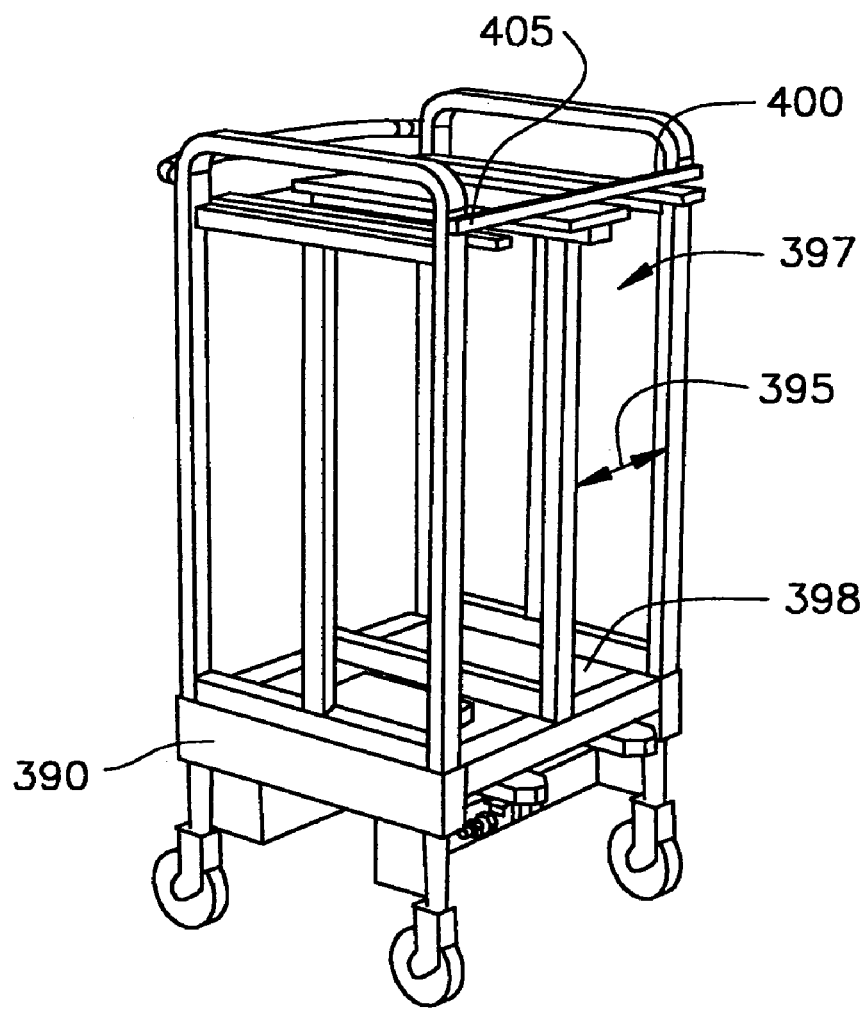
FIG. 5 is another embodiment of a transportation cart which includes a retaining member.

In another example depicted in FIG. 5, a transportation cart 390 includes the features of transportation cart 290 except it includes two slots and further includes a retaining bar 400. Frame 15 is received in a channel 397 having a dimension 395 and a bottom 398. Retaining bar 400 may be reconnected to cart 390 at a first end 405 via a pivot or pin. After frame 15 has been inserted into channel 397, retaining bar 400 may be closed to retain frame 15 therein. Also, cart 290 and/or cart 390 may include wheels to allow movement thereof with such wheels being lockable to prevent movement when desired.

In an example not depicted, a cart, similar to cart 290, may enclose an interior portion (not shown) and may have insulated walls (not shown) and an insulated floor (not shown) for reducing heat losses during storage or transportation of one or more frames 15 holding one or more flexible containers 10. Cart 290 may also include one or more doors (not shown) to allow access to an interior (not shown) thereof and an insulated top (not shown) may be fixedly or removably attached to cart 290. In addition, for long term storage of the biopharmaceutical product contained in flexible container 10, in either a liquid or a frozen state, a walk-in, a chest or a cabinet chiller or freezer (not shown) can be equipped with rails or channel supports or support rails (not shown) adapted to receive frames 15. Such rails or supports may also be at a same height relative to rails 292 to facilitate movement therebetween by a user.

Further, such rails or supports for supporting frames (e.g. frame 15) may be located at various locations around a facility for processing biopharmaceutical materials. For example, a pair of rails may be arranged on a scale for receiving a frame. Such an arrangement on a scale allows an increase in weight of a frame holding a flexible container to indicate a certain volume of biopharmaceutical material as such biopharmaceutical material is introduced into the flexible container. The use of weight to determine such a volume of biopharmaceutical material in container 10 may facilitate repeatability and accuracy in filling the flexible containers supported by the frames on a scale. Also, such rails might be located in other locations to allow long or short term storage of biopharmaceutical materials in containers 10 supported by frames 15. For example, rails or supports may be present in freezers, stations for processing unfrozen biopharmaceutical materials, or other such locations where it is desirable to have flexible containers 10 held by frames 15, but for which it is not desired to have the biopharmaceutical materials held in a temperature control unit (e.g., temperature control unit 20) or in a transportation cart (e.g., cart 290). Further, such rails may be identical to rails 292 but they may be part of a scale 1500 as depicted in FIG. 27. More specifically, scale 1500 may include scale supporting rails 1510 and a channel 1520 for receiving frame 15. Scale 1500 may also include a display 1530 for displaying a weight of the biopharmaceutical material included in flexible container 10. A weight determining portion 1540 may determine the weight of the biopharmaceutical material based on the weight of the components of scale 1500 and the increased weight due to the biopharmaceutical materials. Other examples of rails being utilized in a stationary position include such rails being mounted to a floor or other surface of a processing facility. Such rails may consist of a structure identical to cart 290 but with the wheels thereof removed, for example. Further, scale 1500 may include any type of means of determining and displaying a weight of an object received thereon, for example, springs, digital displays, analog displays, or any type of weight sensors.

Flexible container 10 (FIG. 6) may be formed of a laminated film which includes a plurality of layers and may have an interior volume ranging from 0.01–100 liters, for example. Further, flexible container 10 could be available in a variety of sizes to accommodate different uses, for example, 8.3 and 16.6 liter flexible containers may be utilized. Also a biocompatible product-contacting layer of the interior of flexible container 10 may be formed of a low density polyethylene, very low density polyethylene ethylene vinyl acetate copolymer, polyester, polyamide, polyvinylchloride, polypropylene, polyfluoroethylene, polyvinylidenefluoride, polyurethane or fluoroethylenepropylene, for example. A gas and water vapor barrier layer may also be formed of an ethylene/vinyl alcohol copolymer mixture within a polyamide or an ethylene vinyl acetate copolymer. Further, flexible container 10 may include a layer with high mechanical strength (e.g. a polyamide), and an external layer with insulating effect to heat welding, for example, polyester. The layers may be compatible with warm and cold conditions and may be able to withstand ionizing irradiation for sterilization purposes. Also, flexible container 10 may have a large surface area to volume ratio, and a relatively thin wall thus promoting heat transfer therethrough when received in temperature control unit 20. One example of materials useful for formulation of flexible container 10 is described in U.S. Pat. No. 5,988,422 to Vallot, the entire subject matter of which is hereby incorporated herein by reference. Also, flexible container 10 may be disposable, thus promoting ease of use and preventing cross-contamination of the interior of flexible container 10 which might result when reusing other types of containers.

Container 10 may be adapted to receive and contain frozen and/or liquid biopharmaceutical materials. In an embodiment, the biopharmaceutical materials may comprise protein solutions, protein formulations, amino acid solutions, amino acid formulations, peptide solutions, peptide formulations, DNA solutions, DNA formulations, RNA solutions, RNA formulations, nucleic acid solutions, nucleic acid formulations, antibodies and their fragments, enzymes and their fragments, vaccines, viruses and their fragments, biological cell suspensions, biological cell fragment suspensions (including cell organelles, nuclei, inclusion bodies, membrane proteins, and/or membranes), tissue fragments suspensions, cell aggregates suspensions, biological tissues in solution, organs in solution, embryos in solution, cell growth media, serum, biologicals, blood products, preservation solutions, fermentation broths, and cell culture fluids with and without cells, mixtures of the above and biocatalysts and their fragments.

Figure 6:
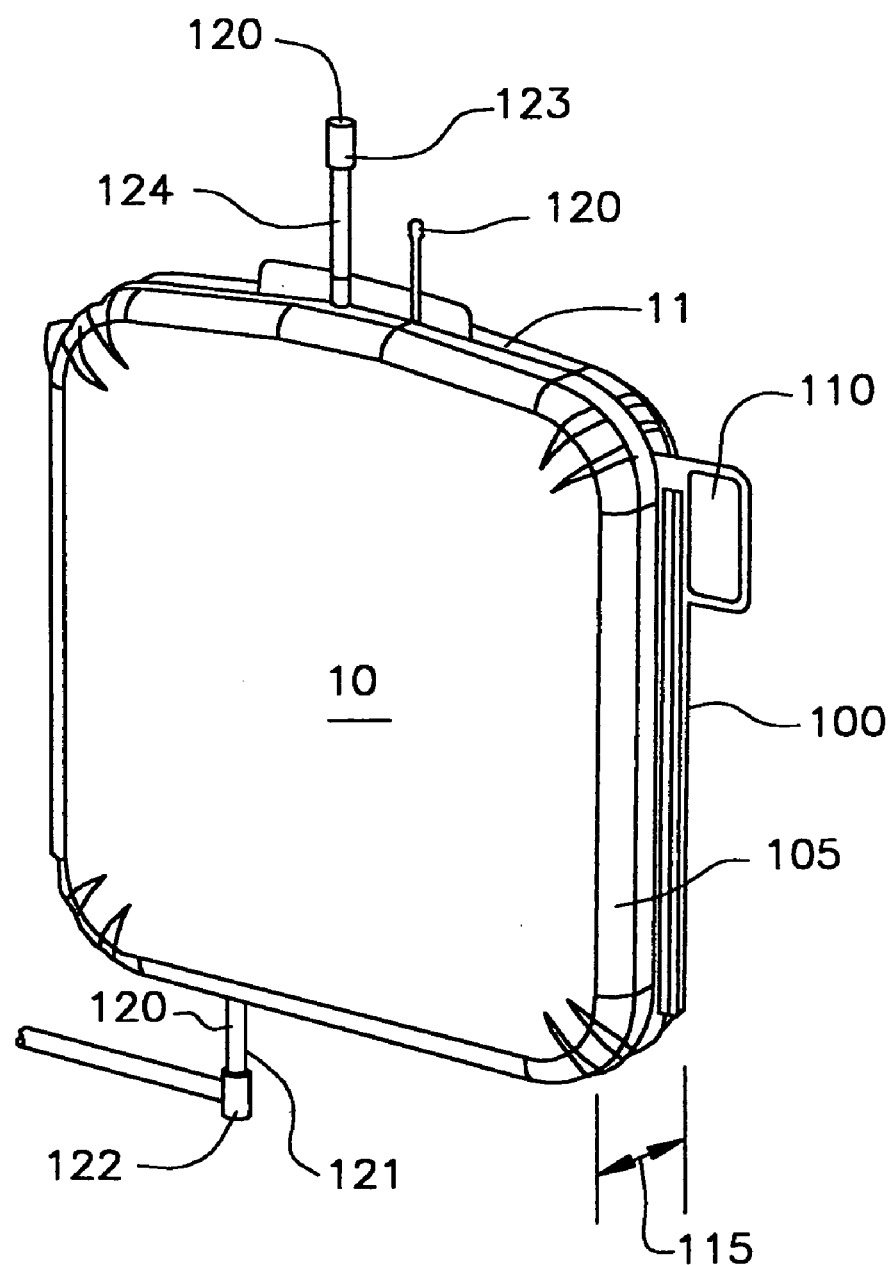
FIG. 6 is a perspective view of a flexible container for receiving biopharmaceutical materials.
Figure 8:
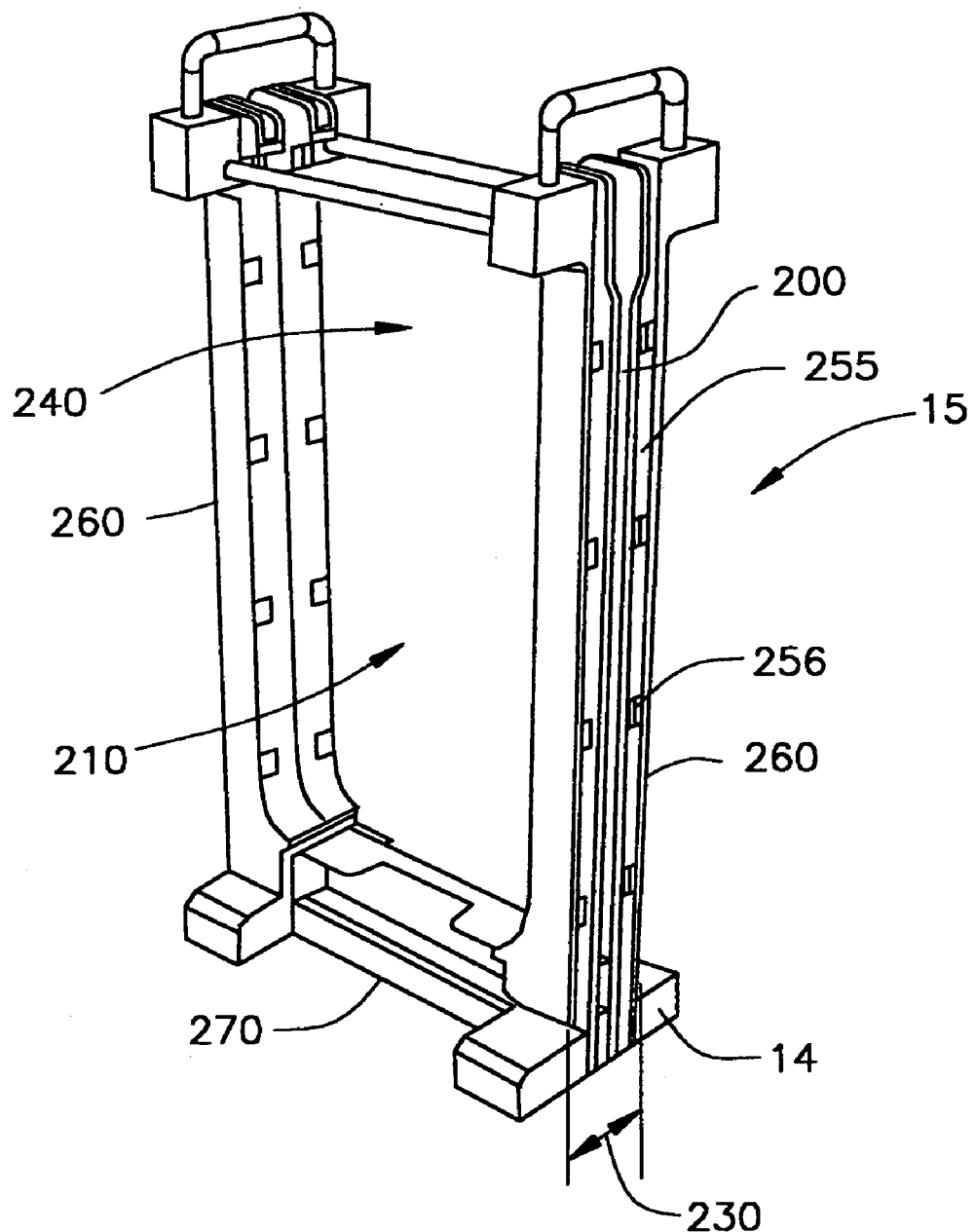
FIG. 8 is a perspective view of a frame for receiving the flexible container of FIG. 6.
Figure 9:
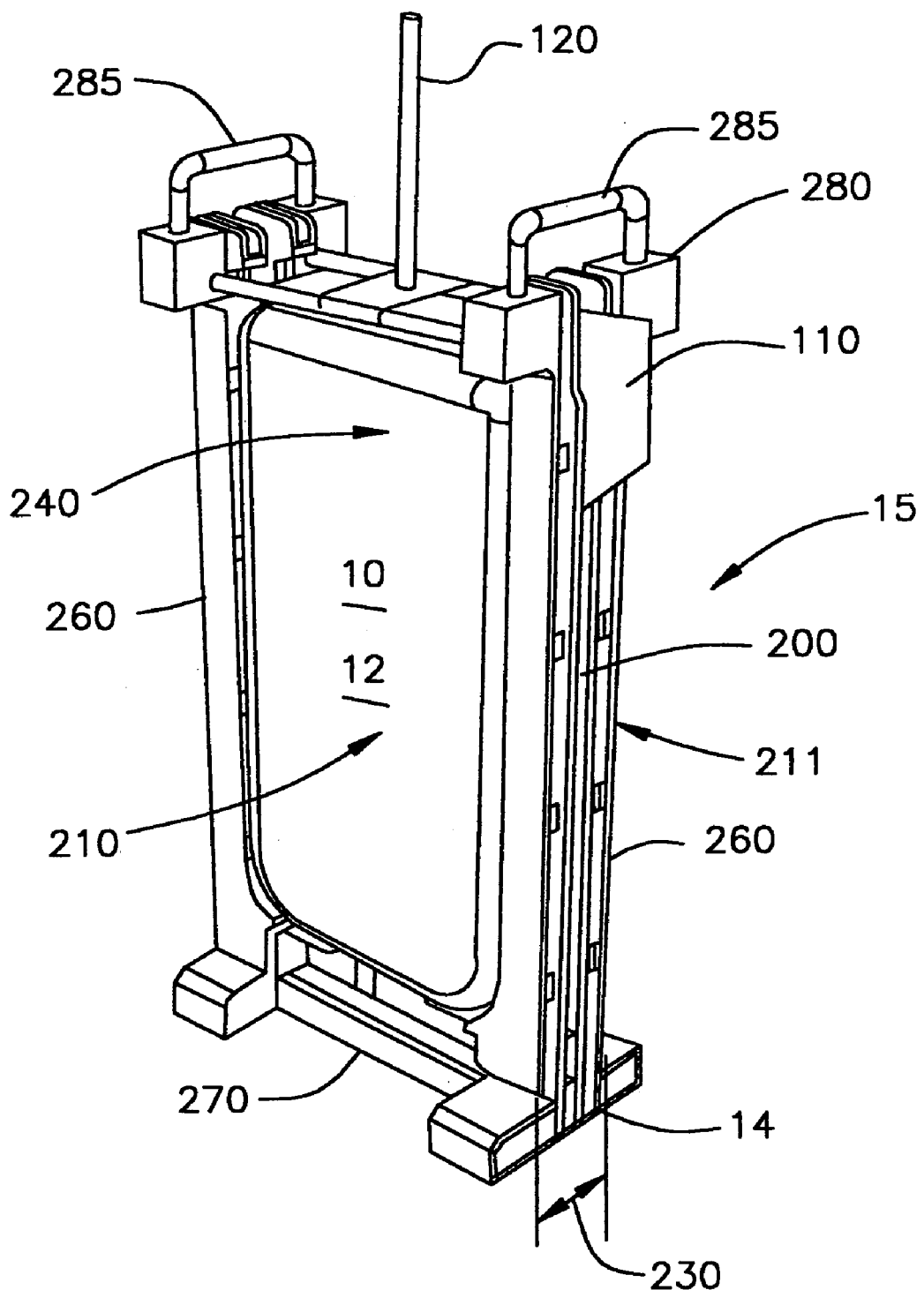
FIG. 9 is a perspective view of the flexible container of FIG. 6 being received in the frame of FIG. 8.

Sterile, flexible container 10 may be adapted to be received in frame 15 for supporting flexible container 10. For example, flexible container 10 may include an outwardly-extending flange 100 adapted to be received in a frame channel 200 of frame 15, as depicted in FIGS. 6, 8 and 9. For example, flange 100 could be a plastic reinforcement rod dimensioned to be received in channel 200. Thus, flange 100, and therefore flexible container 10, may be inserted vertically downward or removed vertically upward, but may not be moved laterally or in directions other than up and down due to the engagement of flange 100 with channel 200. Thus, flange 100 serves to support the flexible container 10 laterally, retain a shape of flexible container 10 during filling thereof, reduces sagging of container 10 and ensures dimensional stability of flexible container 10 by spreading a load placed thereon along three different sides of flexible container 10, i.e., both sides and the bottom thereof.

Further, flexible container 10 may include a horizontally extending flange or rod (not shown) attached to a topside 11 of flexible container 10. The horizontally extending flange may be configured to be received in channel 200 and may be substantially perpendicular to flange 100. The horizontally extending flange also may be configured to connect to a top portion of frame 15 to reduce sag of flexible container 10 when flexible container 10 is received in frame 15.

Flexible container 10 may also include a display tab 110 or other means for receiving a label to provide an indication to a user as to the contents of flexible container 10. Such a label may include written information, an embedded microchip, a RF transmitter and/or an electronic or magnetic bar code for indication of the contents of flexible container 10 to facilitate identification, tracking, and/or characterization of the contents thereof. The use of the label may thus simplify management of materials stored in flexible container 10, received in frame 15, when it is stored in a large freezer (e.g., walk-in, a chest or a cabinet chiller or freezer (not shown)) containing other frames and flexible containers which may appear similar thereto.

As shown in FIG. 6, flexible container 10 may include one or more ports or conduits 120 to allow filling or draining of biopharmaceutical materials or other solids, liquids, or gases into and/or out of interior (not shown) of flexible container 10. Conduits 120 may also be used to insert a measurement probe (not shown) inside flexible container 10 (e.g., a pH electrode, a conductivity sensor, temperature probe, an ion selective electrode, a spectophotometric probe, an ultrasound sensor, an optic fiber.) Conduits 120 may be positioned in the top part of the container and/or in the bottom part of flexible container 10. The position of the conduits may facilitate filling and/or drainage of the containers. Conduits 120 may be integral to flexible container 10 or it may be connectable to a receiving port (not shown) thereof. For example, conduits 120 could be connected to a receiving port using a fitting placed within the inlet port. Fittings such as those described in U.S. Pat. No. 6,186,932, may be used for the connection of such conduits. Also, fittings which can maintain the sterility of the contents of the container or flexible container may preferably be used. The fittings may be configured in different shapes, such as straight fittings and/or angled fittings including ninety (90) degree elbows, if desired. In another example, conduits 120 may include a filter (not shown) to filter any impurities or other undesirable materials from the biopharmaceutical material.

For example, one of conduits 120 may be a drainage conduit 121 on a bottom portion of container 10. Drainage conduit 121 may include a clamp 122 or a valve (not shown) to allow the selective drainage of container 10. Drainage conduit 121 may further be formed of any of various lengths to allow efficient drainage of container 10. In one example, drainage conduit 121 may be of a length such that it may be received in a conduit-receiving groove 255 of frame 15. More specifically, conduit 121 may be of a length allowing it to be extended from the bottom of container 10 to a side of container 10, to the top of frame 15, and back to a bottom of frame 15 in groove 255. Groove 255 may further include retaining members 256 spaced along its length which drainage conduit 121 may be inserted under. Retaining members 256 may extend a portion of a distance across groove 255 (FIG. 8) such that drainage conduit 121 may be inserted under retaining member 256 but retaining member 256 may inhibit movement of drainage conduit 121 from groove 255. In another example, one of conduits 120 may include a sleeve (not shown) extending from an exterior of container 10 into an interior thereof such that a temperature probe or other sensing device may be inserted into such sleeve to allow measurement of biopharmaceutical material held in container 10. One example of such a temperature sensor is a resistance temperature detector. In another example, a first top conduit 124 of conduits 120 may include a clamp 123 or a valve (not shown) to allow selective filling and/or draining of the biopharmaceutical material therethrough in a manner similar to drainage conduit 121 and clamp 122.

Figure 7:
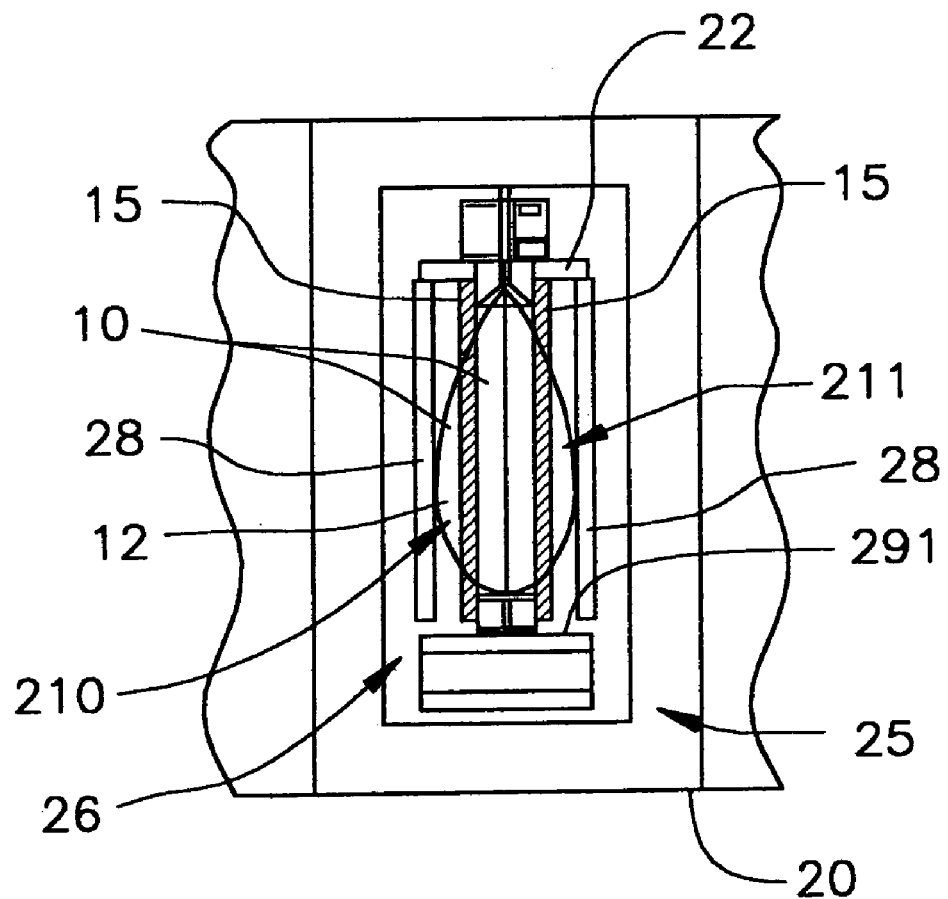
FIG. 7 is a side cross-sectional view of a slot of the temperature control unit of FIG. 3.

Temperature control unit 20 is configured to control the temperature of interior 26 and control unit slots 25 thereof, as depicted in FIGS. 2 and 7. Also, temperature control unit 20 may include therein, or may be coupled to, a controller (not shown) to allow a user to control the heating, cooling, freezing or thawing, for example, of the biopharmaceutical materials in flexible container 10, when it is inserted into slots 25 of interior 26 of temperature control unit 20. Heating, cooling, freezing or thawing of the contents of flexible containers 10 placed inside temperature control unit 20 may be controlled by blowing a continuous stream of cold or warm air, by direct contact of the containers with cold or warm surfaces, or by spraying cooling fluid (e.g., liquid nitrogen), for example.

In a preferred embodiment, temperature control unit 20 is a heat exchanger having one or more conduction plates for heating and/or cooling flexible container 10 and biopharmaceutical materials contained therein, as best depicted in FIG. 7, which illustrates a front cross-sectional view of one of slots 25 of interior 26. For example, temperature control unit 20 may include plates 28 for contacting flexible container 10 to cool or heat the contents thereof. Also, one or more of plates 28 may be moveable toward each other with container 10 therebetween to compress flexible container 10 when flexible container 10 is received in frame 15 and frame 15 is received in slot 25 of temperature control unit 20. Further, plate 28 could be stationary and temperature control unit 20 may include one or more non-temperature controlled moveable walls, surfaces, or plates (not shown) configured to compress flexible container 10, when flexible container 10 and frame 15 are received in slot 25. Alternatively, plates 28 may be movable along with such additional movable walls, surfaces, or plates (not shown).

Frame 15 may be formed to receive and support flexible container 10 to provide additional rigidity and support to flexible container 10, thus facilitating handling, storage, transportation, and/or temperature control thereof as depicted in FIGS. 8 and 9. Frame 15 may include a first opening 210 and a second opening 211 on an opposite side of frame 15 from opening 210. These openings expose a large surface area of flexible container 10 to interior 26 of temperature control unit 20. Through these openings, flexible container 10 may contact heat transfer surfaces such as plates 28 (FIG. 7), air at a controlled temperature, or liquid cooling spray within temperature control unit 20. For example, a first side 12 (FIG. 7) of flexible container 10 may contact a heat transfer surface (e.g., one of plates 28) of interior 26 of temperature control unit 20 (FIGS. 3 and 7) through opening 210 to control the temperature of the biopharmaceutical material in flexible container 10. Alternatively, side 12 of flexible container 10 may be exposed to a still or circulating air within temperature control unit 20. For example, the biopharmaceutical material may be frozen or thawed while in flexible container 10, when flexible container 10 is received in frame 15 and frame 15 is received in slot 25 of temperature control unit 20.

Also, flexible container 10 may be adapted to be compressed by plates 28, (FIG. 7) of temperature control unit 20, when substantially filled with the biopharmaceutical material, and flexible container 10 and frame 15 are received in interior 25. Further, the contents of flexible container 10 may be frozen or solidified while plates 28 are compressing it in temperature control unit 20 to cause flexible container 10 to have a dimension or width 115 in a direction between first opening 210 and second opening 211 of frame 15, which is less than or equal to a dimension or width 230 of an interior 240 of frame 15 in the same direction as dimension 115, as depicted in FIGS. 6 and 8. Thus, flexible container 10 having the biopharmaceutical material frozen therein may be confined within an envelope or thickness defined by frame 15. By compressing flexible container 10 in frame 15, a substantially rectangular cross-sectional profile is created of flexible container 10 having the biopharmaceutical material therein. Such a cross-sectional profile promotes contact between flexible container 10 and heat transfer plates 28. This is particularly true in the corners of flexible container 10, thus allowing freezing to proceed in a uniform manner in a direction normal to plates 28. Further, the compression of flexible container 10 may force the biopharmaceutical material in flexible container 10 to occupy any voids or spaces between plate 28 and flexible container 10. By reducing or minimizing such voids or spaces, contact of plate 28 with flexible container 10 may be more uniform and thus cause more uniform cooling of the biopharmaceutical material contained in flexible container 10. Alternatively, the biopharmaceutical material may be heated or thawed in temperature control unit 20 through such contact with plates 28.

Frame 15 may further include upwardly extending sides 260, a bottom 270 and a top 280 to protect and support flexible container 10. Also, top 280 may include one or more handles 285, as best depicted in FIGS. 8–9. Frame 15 may preferably be formed of materials which remain stable and retain their structural properties. Specifically, such materials should retain their load-bearing capacity and exhibit glass transition temperatures no higher than negative 80 degrees Celsius while being resistant to cleaning agents and methods commonly used in biopharmaceutical manufacturing, e.g., sodium hydroxide, sodium hypochloride (CLOROX), peracetic acid, etc.

For example, sides 260 may be formed of fluoropolymer resin (i.e. TEFLON) and top 280 and bottom 270 may be formed of stainless steel. Also, sides 260, bottom 270 and/or top 280 may be made of any number of other materials including aluminum, polyethylene, polypropylene, polycarbonate, and polysulfone, for example. Further materials may include composite materials such as glass-reinforced plastic, carbon-fiber reinforced resins, or other engineering plastic materials known to offer high strength-to-weight rations and which are serviceable at various temperatures of interest. It will be understood by those skilled in the art that sides 260, bottom 270 and/or top 280 may be monolithic and integrally formed as one piece or suitably connected together. Further, sides 260, bottom 270 and/or top 280 could be formed of a same material (e.g. stainless steel) or they could be formed of different materials and connected together. Frame 15 may also include one or more foot members 14 for maintaining frame 15 in an upright position. As will be understood by those skilled in the art, foot members 14 may be integral to or connectable to one or more sides 260 of frame 15.

Figure 10:
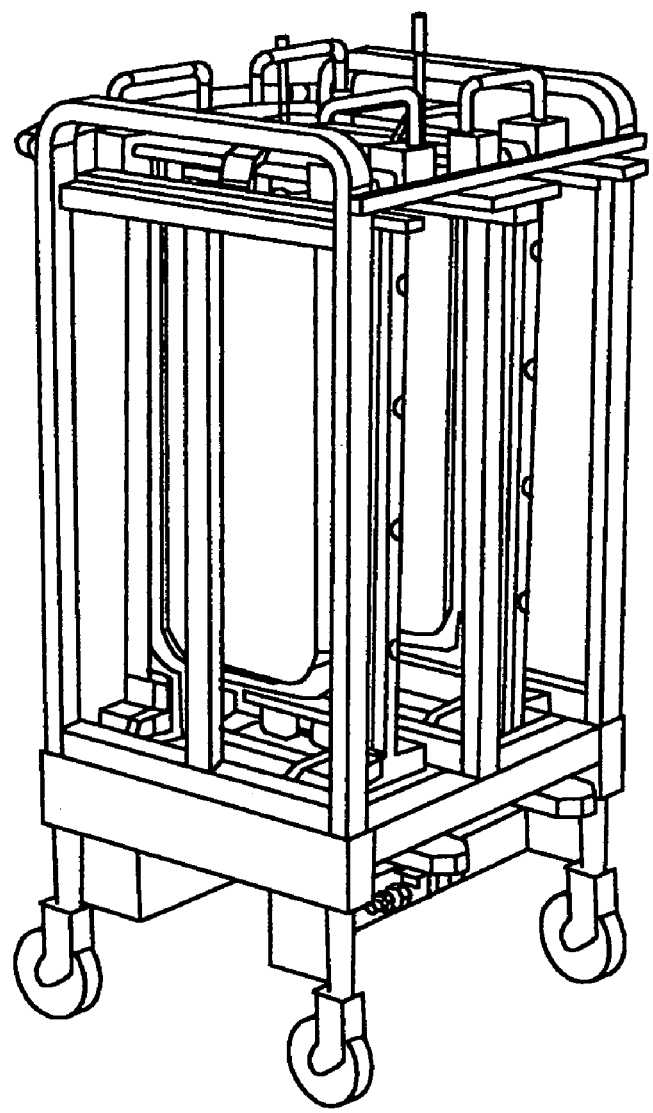
FIG. 10 is a perspective view of the transportation cart of FIG. 5 receiving two of the frames depicted in FIG. 8 holding the container of FIG. 6

Frame 15 may secure flexible container 10 in a defined position as illustrated in FIG. 9. Such arrangement facilitates the handling and transportation of liquid filled flexible container 10. In particular, the filling and drainage operation are facilitated by the self-standing position of flexible container 10 supported by frame 15, when supported by foot members 14. Alternatively, flexible container 10 may be filled and/or drained while frame 15 having flexible container 10 therein is located inside cart 290 as depicted in FIG. 10. As described above, sides 260 of frame 215 may include grooves 255 for receiving conduits (e.g., drainage conduit 120) therein. These grooves allow for the compact storage of such conduits when they are not in use. Retaining members 256 promote the retention of such conduits in grooves 255 to allow such compact storage. In one example, when it is desired to drain flexible container 10, drainage conduit 121 may be removed from groove 255 by maneuvering conduit 121 around retaining members 256. Clamp 122 or a valve (not shown) may then be open to allow such drainage by gravity or via a pump through drainage conduit 121.

Figure 11:
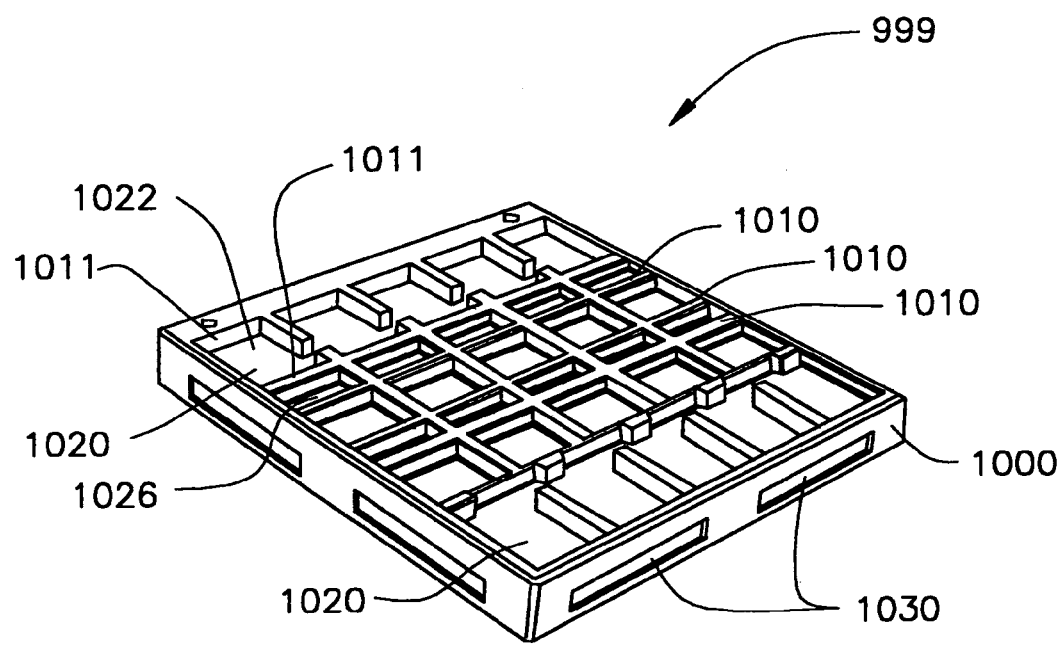
FIG. 11 is a perspective view of another embodiment of a transportation cart, in accordance with the present invention.
Figure 12:
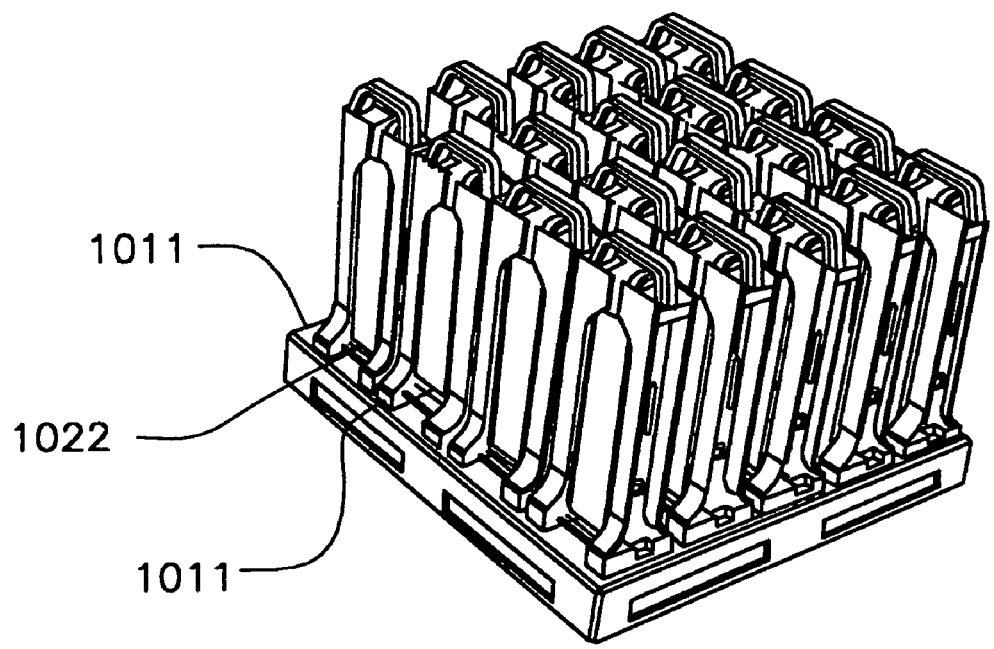
FIG. 12 is a perspective view of the transportation cart of FIG. 1 further including a plurality of frames holding a plurality of flexible containers for receiving biopharmaceutical materials.
Figure 13:
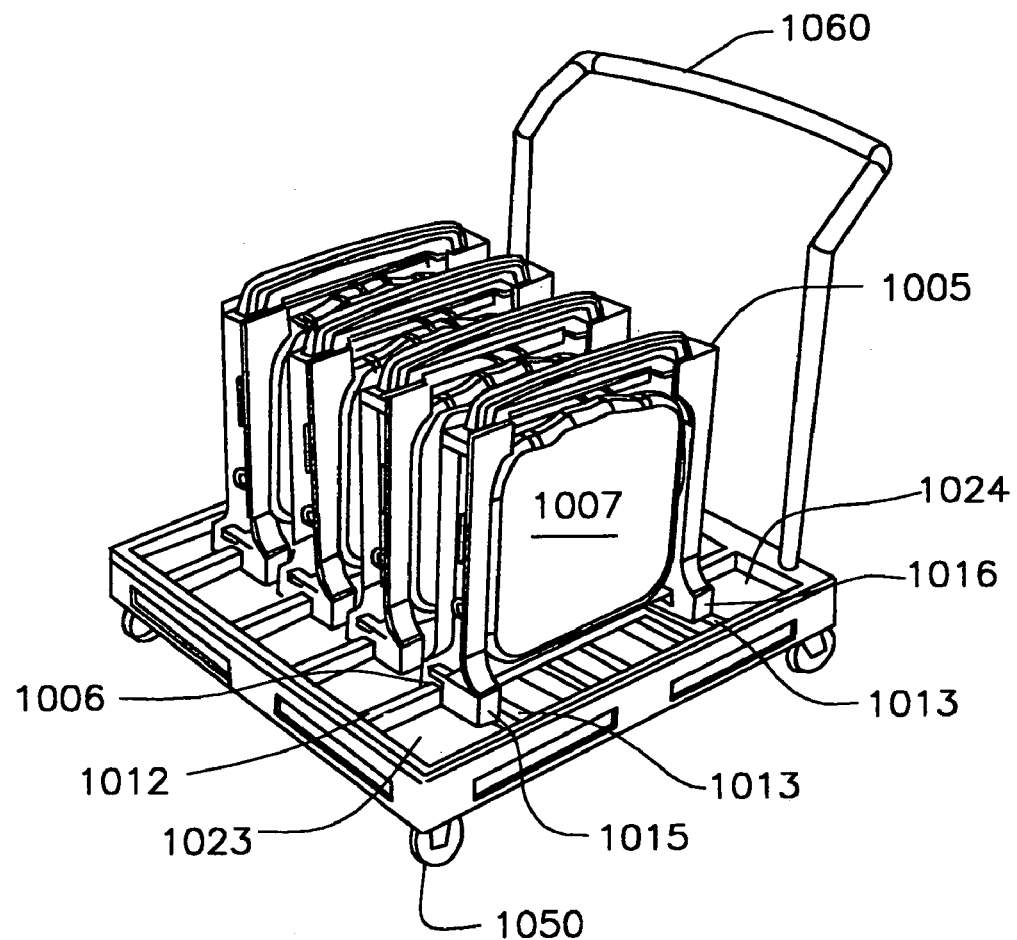
FIG. 13 is a perspective view of the transportation cart of FIG. 11 further including wheels and a handle.

In another embodiment of the present invention, a transportation cart 999 includes a movable cart or platform 1000 having a grid for receiving a plurality of supporting structures, for example frames 15 which support containers for holding biopharmaceutical material, as depicted in FIGS. 11–13. The grid includes a plurality of projections 1010 which protrude from a receiving surface 1020 of movable platform 1000. Projections 1010 may be arranged to allow frames of differing sizes to accommodate different sized containers to be received thereon. Foot members 14 (FIG. 8) of frames 15 may allow frames 15 to stand upright on receiving surface of platform 1000. For example, frame 15 may fit within an opening 1022 between projections 1011. Further, one of foot members 14 may be received in opening 1022 and a second of foot members 14 may be received in a second opening 1026. Alternatively, a larger frame 1005 holding a larger container may have a first foot member 1015 received in an opening 1023 while a second foot member 1016 is received in a second opening 1024. Further, first foot member 1015 and second foot member 1016 may have openings or channels 1006 between respective lateral portions thereof to allow frame 1005 to straddle a projection 1012. Frame 1005 may also be received on receiving surface 1020 on opposite sides of projections 1013 while straddling projection 1012. The projections described may be utilized to reduce or prevent movement of frames 15 or frames 1005 on receiving surface 1020, thus inhibiting the frames from being dislodged and the flexible containers being damaged thereby. Moreover, frames and/or containers of different sizes may be configured in various different ways on platform 1000 to allow efficient storage and transport thereof on cart 999.

Also, platform 1000 may include fork slots 1030 to receive forks (not shown) of a fork lift (not shown) to allow platform 1000 having frames 15 thereon to be transported and/or stored. For example, frames 15 may be individually or collectively transferred via a forklift from one or more temperature control units 20 to a storage freezer (e.g., walk-in freezer) and stored therein on platform 1000. Alternatively, platform 1000 may include wheels 1050 and/or a handle 1060 to allow platform 1000 to be pushed by user to transport frames 15 and containers 10 between one or more temperature control units 20 and the walk-in freezer. Further, platform 1000 may be utilized to move frames 15 and containers 10 to or from a filling station for inserting the biopharmaceutical material into containers 10. Such filling may occur while frames 15 and containers 10 are located on platform 1000, for example. Further, a protective and/or insulating cover (not shown) may be provided to cover the frames and containers while they are received on platform 1000 to insulate and/or protect the frames and the containers.

Figure 14:
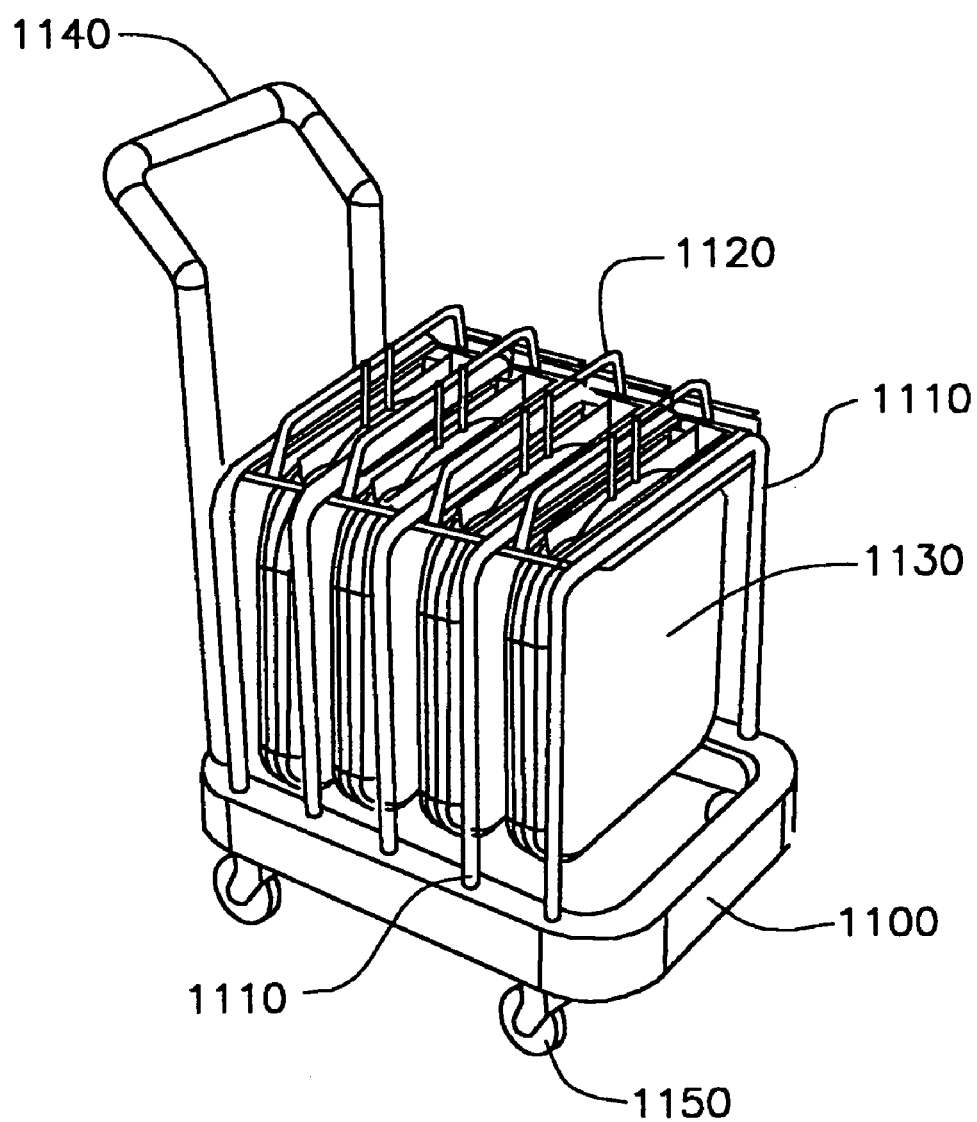
FIG. 14 is a perspective view of a further embodiment of a transportation cart receiving a handle holding a flexible container thereon.
Figure 15:
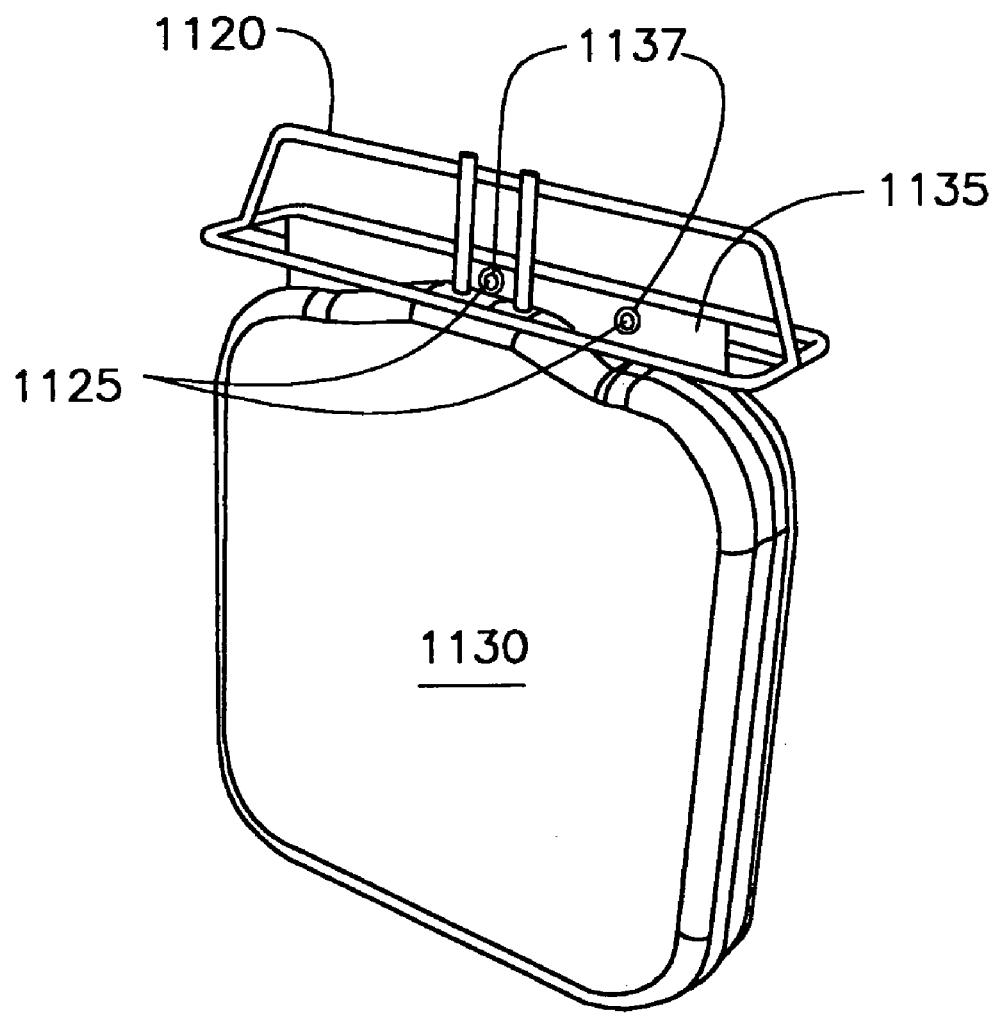
FIG. 15 is a perspective view of the flexible container and handle of FIG. 14.

In a further embodiment of the present invention depicted in FIGS. 14–15, a movable transportation cart 1100 includes a plurality of supporting rails 1110 to support one or more handles 1130 supporting one or more flexible containers 1120 adapted to hold biopharmaceutical material therein during freezing, thawing, transporting, and storing thereof. Handle 1120 may be dimensioned wider than an opening between two of supporting rails 1110 such that handle 1120 having container 1130 attached thereto may rest on supporting rails 1110 to allow container 1120 to be transported on cart 1100. Supporting rails 1110 may be aligned substantially perpendicular to the longitudinal direction of cart 1100 and thus one or more handles 1120 attached to one or more containers 1130 may be aligned in the same manner, as depicted in FIG. 14. Container 1130 may include a flange 1135 having one or more apertures 1137 for receiving one or more posts 1125 of handle 1120 to attach them to each other, as depicted in FIG. 15. Returning to FIG. 14, movable cart 1100 also may be attachable to a cart handle 1140 to allow users to transport the containers received on movable cart 1100. Also, movable cart 1100 may include wheels 1150 to facilitate rolling of movable cart 1100 by a user. In addition to wheels 1150, or as an alternative thereto, movable cart 1100 may include fork slots (not shown) for receiving forks of a forklift (not shown) to allow movable cart 1100 to be transported thereby. For example, movable cart 1100 may be utilized to transport the containers from one or more temperature control units 20 to a walk-in freezer, a filling station for filling containers with biopharmaceutical material, or various other locations.

Figure 16:
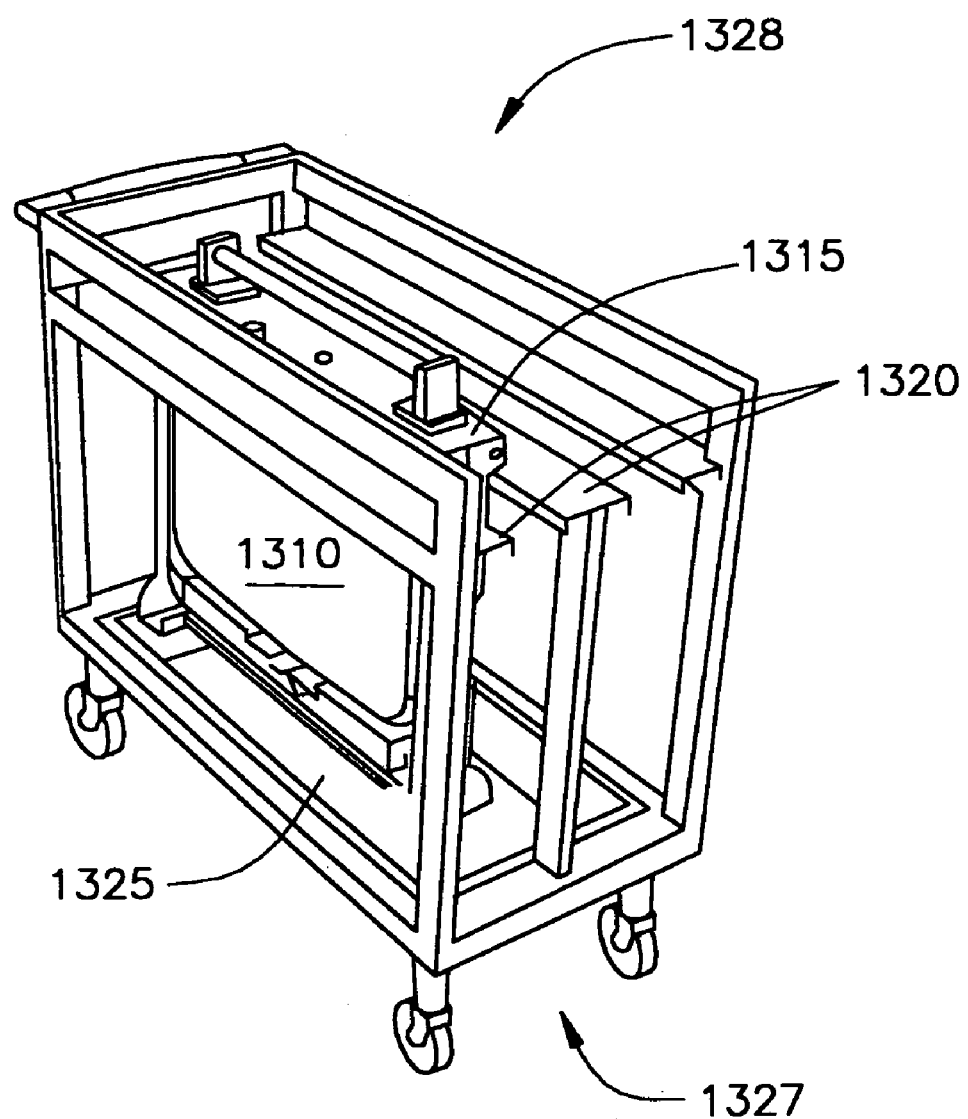
FIG. 16 is a perspective view of another embodiment of a transportation cart receiving a frame holding a flexible container in accordance with the present invention.

In another embodiment of the present invention, a movable transportation cart 1300 may receive a frame 1315 holding a flexible container 1310, as depicted in FIG. 16. Cart 1300 includes rails 1320 to support frame 1315, and which define a channel 1317 for receiving frame 1315. Frame 1315 maybe located on rails 1320 by inserting frame 1315 through a side 1327 or a top 1328 of cart 1300. A drip tray 1325 is also included in cart 1300 to collect biopharmaceutical materials or other liquids which may leak from flexible container 1310 or may otherwise be present on cart 1300. Tray 1325 may be removable to allow disposal of such liquids. Alternatively, drip tray 1325 may include an outlet to allow any collected liquids to be removed therefrom. Such outlet may include a valve (not shown) or other means for allowing selective removal of the liquids when desired. As noted above for cart 290, cart 1300 may be utilized for long or short-term storage of biopharmaceutical material or transportation thereof.

Figure 17:
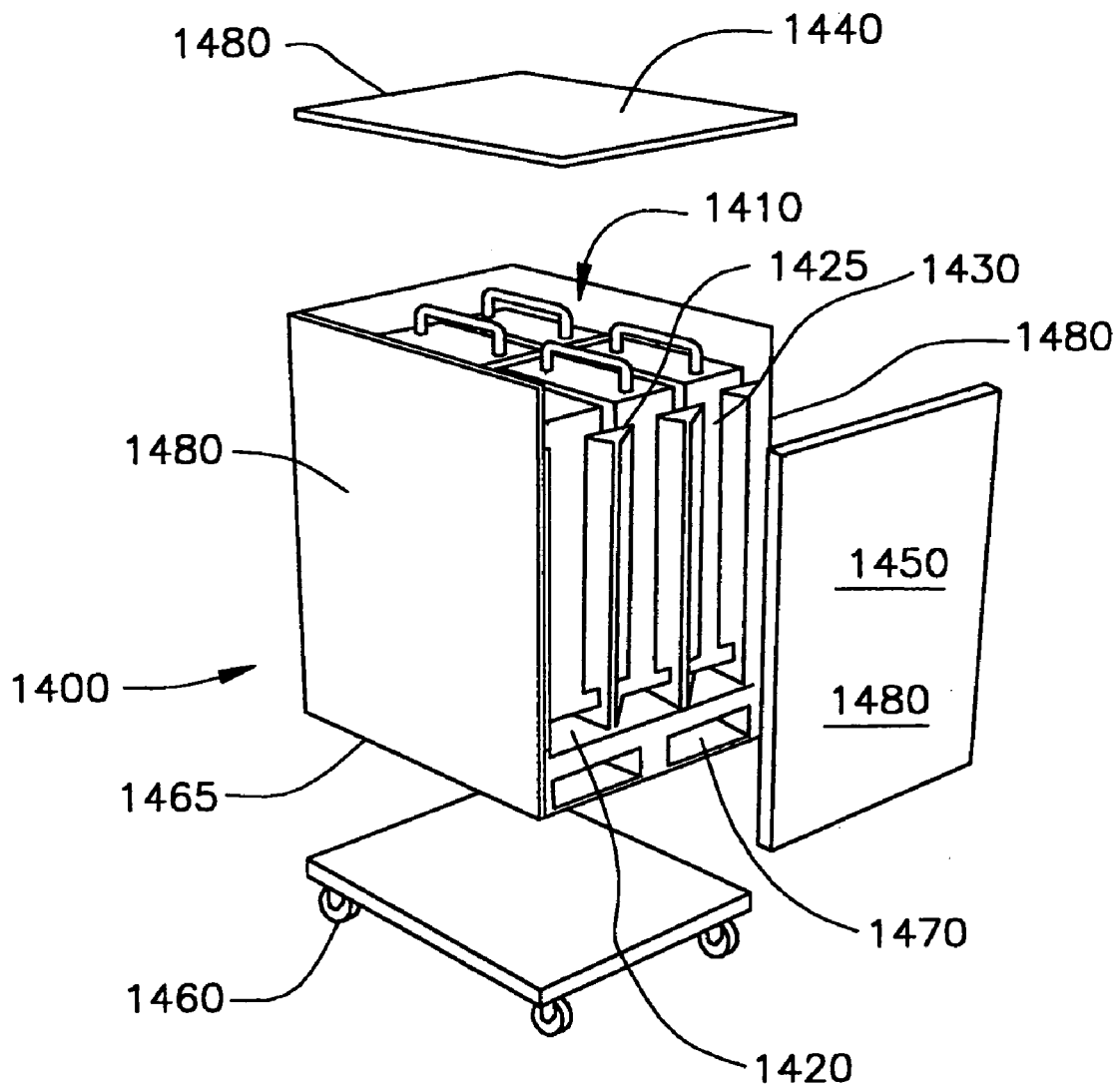
FIG. 17 is perspective view of yet another embodiment of transportation cart receiving a plurality of frames supporting a plurality of flexible containers, in accordance with the present invention.
Figure 18:
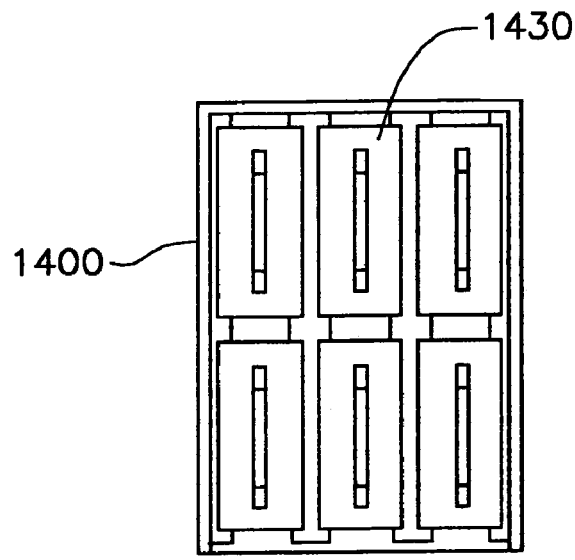
FIG. 18 is a top cross-sectional view of the cart of FIG. 17.
Figure 19:
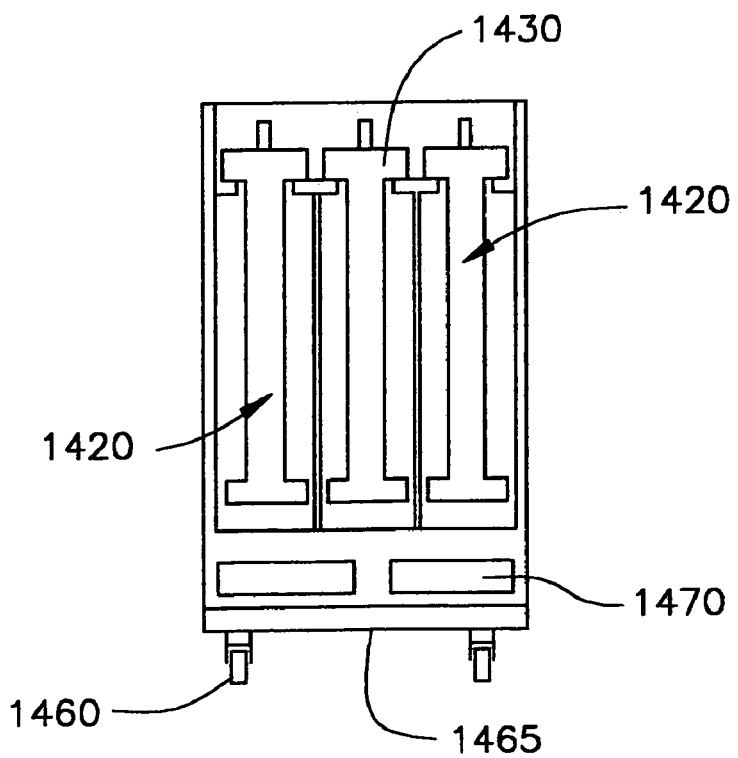
FIG. 19 is a front cross-sectional view of the cart of FIG. 17.
Figure 20:
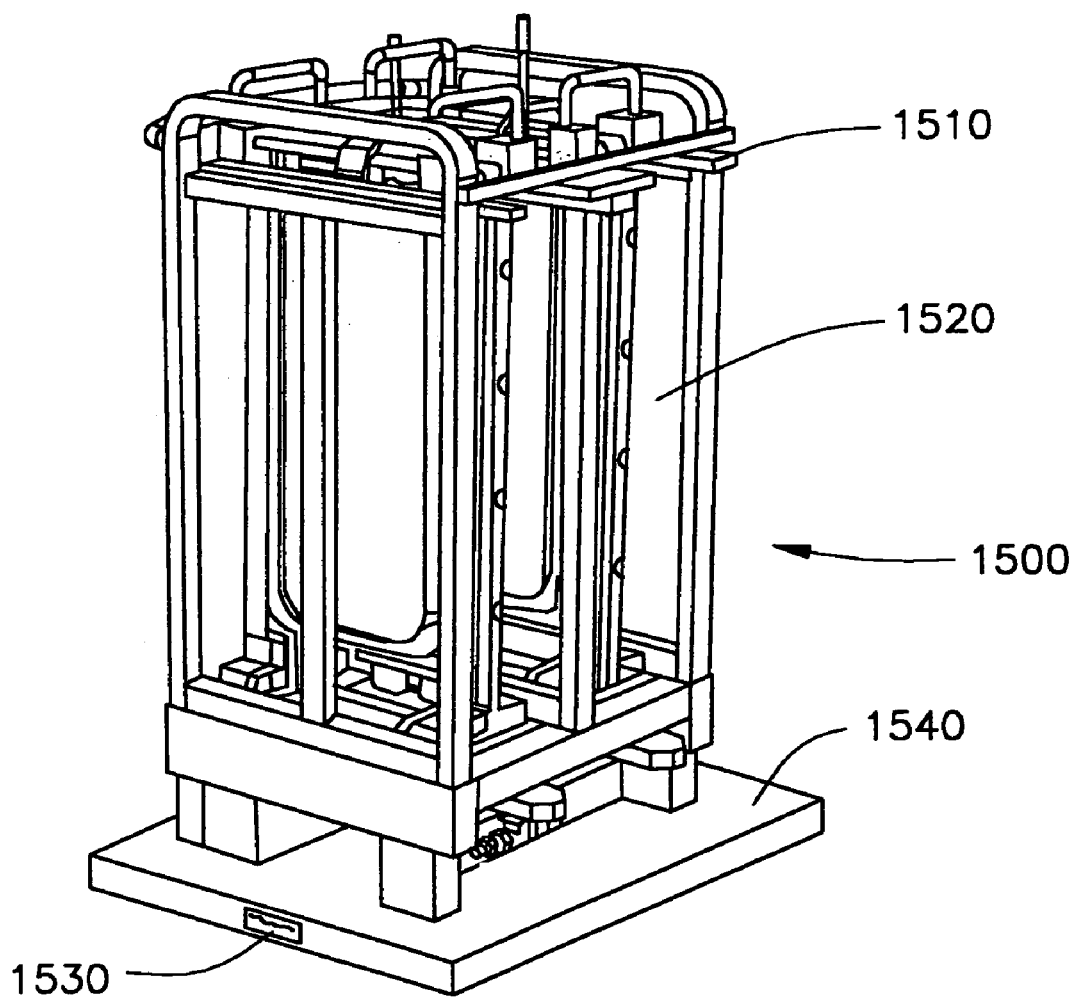
FIG. 20 is a perspective view of a scale having a frame holding a container received thereon.

FIGS. 17–19 depict yet a further embodiment of a movable transportation cart 1400 preferably also useable to store flexible containers and frames 143 with frozen biopharmaceutical material therein, in accordance with the present invention. Cart 1400 includes an interior 1410 having a plurality of channels 1420. Each of channels 1420 may be dimensioned to receive one or more frames 1430 supporting a container (not shown) for receiving biopharmaceutical materials. Further, each of channels 1420 may be dimensioned to receive one of frames 1430 supporting such a container (not shown), when the biopharmaceutical material in the container is in a frozen state. Specifically, the biopharmaceutical material may be frozen in a substantially uniform thickness to allow uniform and compact storing of frames 1430 holding the containers (not shown). Thus, channels 1420 may be dimensioned to allow for such substantially uniform thickness of the frozen biopharmaceutical material in the containers. In particular, biopharmaceutical materials frozen in a uniform matter may take up less space than unfrozen biopharmaceutical material, due to the non-uniform shape which non-frozen biopharmaceutical material may take in a flexible container. For example, a flexible container holding nonfrozen biopharmaceutical material may have a rounded shape due to a lack of support on open portions (e.g., opening 210 and second opening 211) of frame 15 of a frame supporting such flexible container. On the contrary, biopharmaceutical material which is frozen while pressure is being applied to sides thereof (e.g., at first opening 210 and second opening 211) of frame 15 may have a uniform shape due to the presence of plates 28 on the openings during freezing of the biopharmaceutical material. Thus, the uniform nature of the shape which frozen biopharmaceutical material may take when so frozen allows channels 1420 to be narrower than they might be for unfrozen biopharmaceutical material. Alternatively, channels 1420 may be dimensioned to receive frames and/or containers holding such unfrozen biopharmaceutical material. In particular, when channels 1420 are configured to hold such unfrozen biopharmaceutical material, the dimension thereof may be wider than such channels dimensioned to hold an equivalent volume of frozen biopharmaceutical material.

Each of channels 1420 may also include a supporting rail 1425 on each side thereof defining the channel. Each of frames 1430 may be received on and supported by two supporting rails 1425. Frames 1430 may be insertable and removable through a removable top 1440 and/or a removable side 1450. Cart 1400 may be movable via rollers 1460 on a movable platform 1465 attachable to cart 1400. Further, cart 1400 may include slots 1470 for receiving forks (not shown) of a forklift (not shown). Also, cart 1400 may be formed of materials such that multiple carts 1400 may be stacked on top of each other. For example, top 1440 and sides 1480 may be formed and attached to each other to allow cart 1400 to support one or more other carts 1400 on top 1440. Such stacking may be performed using a forklift (not shown). As described for cart 1350, cart 1400 may be utilized for long or short-term storage of biopharmaceutical material or transportation thereof. Also, in an example not depicted, a heater or blower (not shown) may also be attached to, and may be in fluid communication with, an interior 1410 of cart 1400. Thawing of the biopharmaceutical material container in container (not shown) may be facilitated by such a blower or heater.

Although the containers are described herein as flexible containers, the containers may be made of a semi-rigid material such as polyethylene or the like. Such a semi-rigid material may retain its shape and/or stand up by itself when empty and when filled with a biopharmaceutical material. An example of such a container could include a container similar to a standard plastic milk jug. Containers made of such similar semi-rigid materials may benefit from additional rigidity supplied by attachment to a frame, for example. Further, the containers whether formed of a flexible or semi-rigid material, contain outer surfaces which contact the interior surfaces (e.g., heat transfer plates) of a temperature control unit 20 so that there is direct contact between the cooled (e.g., to a subzero temperature) or heated interior surfaces of temperature control unit 20 and the outer surfaces of the container containing biopharmaceutical materials. Alternatively, the outer surfaces of the containers for holding the biopharmaceutical materials may be in contact with air flow in interior 26 of temperature control unit 20 to cause the cooling and/or heating of the containers having the biopharmaceutical materials therein to cause the temperature of the biopharmaceutical materials to be controlled.

The biopharmaceutical material in the flexible containers described above may thus be cooled or otherwise thermoregulated in temperature control unit 20 (e.g., to a sub-zero temperature). When such operation is completed, the flexible containers may be removed from temperature control unit 20 by removing the flexible containers and the frames, or other support structures which the flexible containers are received in or connected to, for example. The frames or other support structures holding the flexible containers may be stored in a large chiller or freezer with an interior air temperature of about negative 20 degrees Celsius, for example.

A typical process of processing and/or preserving a biopharmaceutical material is described as follows. Flexible container 10 is inserted into frame 15 as depicted in FIGS. 9–10. Also, frame 15 may be placed in transportation cart 290 (FIG. 1) and transported to a filling station (not shown) where biopharmaceutical material, for example liquid biopharmaceutical material, is inserted through conduit 120 into flexible container 10. In one example, frame 15 may be slid from transportation cart 290 to scale supporting rails 1510 (FIG. 27) of a scale 1500. Flexible container 10 may then be filled to a certain weight determined by the scale. After filling in either manner, flexible container 10, while held in frame 15, is inserted into temperature control unit 20, as shown in FIG. 3. The biopharmaceutical contents are frozen in temperature controlled unit 20 in a controlled manner (e.g., to negative 20 degrees Celsius or below), for example, such that the freeze rate (including the dendritic freeze front velocity from the sides of the container to the center) is controlled within upper and lower limits, as described in U.S. patent application Ser. No. 09/905,488. Thus, cryoconcentration of the biopharmaceutical material is prevented or inhibited, thereby preventing undesirable degradation of the biopharmaceutical material.

After the biopharmaceutical material in flexible container 10 is frozen, flexible container 10 may be removed from the temperature control unit 20 manually by a user and placed in cart 290. Further, frame 15 may be moved into a cart interior 299 of cart 290 and more specifically frame 15 may be received in cart channel 297 and may rest on support rails 292. Alternatively, frame 15 may be advanced to rest on a bottom surface 298 of cart 290 between support rails 292. Thus, frame 15 may be easily moved from slot 25 of interior 26 of temperature control unit 20 to cart 290 by sliding frame 15, when temperature control unit 20 and cart 290 are located adjacent to each other. Cart 290 with frame 15 therein may then be transported to a large freezer, for example, a walk-in freezer having an interior air temperature of about negative 20 degrees Celsius, as is typically present in large medical institutions (e.g., hospitals).

It will be evident to those skilled in the art from the above description that other flexible containers may have their contents frozen or their temperature otherwise regulated and stored in the same manner as flexible container 10. Further, it will be evident that various frames might be utilized to support various containers and to be received in temperature control unit 20 along with being supportable by supporting structures in the transportation carts described above. Examples of such frames and containers are described in U.S. patent application Ser. No. 10/254,025, filed on Sep. 23, 2002 and titled "Systems and Method for Freezing and Storing Biopharmaceutical Material". Also, various temperature control units might be utilized to cool, heat, and/or compress biopharmaceutical material held in flexible containers and/or frames received in such temperature control units. Examples of such temperature control units are described in co-owned U.S. patent application Ser. No. 10/455222, filed consecutively, entitled "Systems and Methods for Freezing, Mixing and Thawing Biopharmaceutical Material". Further, it will be evident that various transportation carts (e.g., cart 1400, cart 1325 or cart 1300) or devices may be utilized to carry out the method described for container 10. Moreover, from the present description, it will be further understood by those skilled in the art that modifications may be made to the specific examples described herein and the steps for performing the method for preserving, freezing, and/or processing the biopharmaceutical material.

Further, the above described flexible containers may be removed from a freezer or other system for storage of the flexible containers and contents thereof at a controlled temperature. These flexible containers having biopharmaceutical material therein may then be received in a temperature control unit for heating, melting, and/or thawing the biopharmaceutical material contained in the flexible containers.

From the above description, it will be understood to one skilled in the art that the flexible containers described herein may be adapted for use in containers, frames, storage units, support structures, transportation carts, temperature control units, heat exchangers, and/or processors of various shapes or sizes. Further, the frames, containers, support structures, heat exchangers, temperature control unit, and/or processors may be adapted to receive flexible containers of various shapes or sizes. These frames or support structures may be adapted for long or short term storage of the flexible containers containing biopharmaceutical materials in liquid or frozen state, or may be adapted to transport the flexible containers containing biopharmaceutical materials in liquid or frozen state. For example, the storage units or transportation carts may be insulated to allow the material to remain at a given temperature for a prolonged period of time. Furthermore, these transportation carts, flexible containers, frames, containers, support structures, temperature control units, heat exchangers, and/or processors may be adapted for utilization with materials other than biopharmaceutical materials. Also, the transportation carts may be equipped with various transport mechanisms, such as wheels, glides, sliders, dry-ice storage compartments, temperature monitoring, pump and accessories, or other devices to facilitate transport and organization thereof. The transportation carts may also include any number of slots for receiving multiple frames holding multiple containers for transport and/or storage thereof. Further, the transportation carts may be adapted to be received in other transportation systems such as, for example, airplane transport containers.

While the invention has been depicted and described in detail herein, it will be apparent to those skilled in the relevant art that various modifications, additions, substitutions and the like can be made without departing from the spirit of the invention and these are therefore considered to be within the scope of the invention as defined in the following claims.

The invention claimed is:

1. A system for transporting and storing a biopharmaceutical material, said system comprising:
   a supporting structure configured to support a container of biopharmaceutical material;
   a connecting structure releasably connecting said container of biopharmaceutical material to said supporting structure;
   said container being sealed to preserve biopharmaceutical material held therein;
   a channel configured to receive said supporting structure and said container of biopharmaceutical material; and
   at least one support rail configured to support said supporting structure and said container in said channel.

2. The system of claim 1 wherein said supporting structure comprises a frame for supporting the container and said at least one support rail is configured to support said frame.

3. The system of claim 1 wherein said at least one support rail is aligned substantially parallel to a longitudinal direction of said channel.

4. The system of claim 2 wherein said channel is engageable with a temperature control unit to allow said frame to be moved onto said at least one support rail from the temperature control unit and to allow said frame to be moved from said at least one support rail into the temperature control unit.

5. The system of claim 4 wherein said channel comprises a bottom side and wherein said bottom side is at a substantially same height relative to a bottom side of a cavity of the temperature control unit.

6. The system of claim 4 wherein the temperature control unit comprises a support member for supporting the frame and wherein said at least one support rail and said support member have a substantially same height relative to each other.

7. The system of claim 4 further comprising at least one alignment tab engageable with the temperature control unit to align the channel with a slot of the temperature control unit.

8. The system of claim 7 wherein the at least one alignment tab is engageable wit a recess of the temperature control unit to align said at least one support rail with a support member of the slot of the temperature control unit.

9. The system of claim 1 further comprising a forklift slot for receiving a fork of a forklift to allow the container to be moved by the forklift.

10. The system of claim 1 further comprising a drip tray for collecting liquids.

11. The system of claim 10 wherein said drip tray comprises a selectively openable outlet.

12. The system of claim 1 further comprising a wheeled structure connected to said at least one support rail to allow the biopharmaceutical material to be transported.

13. A system for freezing, storing, transporting or thawing a biopharmaceutical material, said system comprising:
    a frame configured to support a container of biopharmaceutical material;
    a temperature control unit having a slot configured to receive said frame supporting said container; arid
    a movable cart having a channel therein, said channel configured to receive said frame supporting said container.

14. The system of claim 13 wherein said slot comprises a first bottom side and said channel comprises a second bottom side, and wherein said first bottom side and second bottom side are at a substantially some height relative to each other.

15. The system of claim 13 wherein said channel comprises at least one support rail for supporting said frame, said slot comprises a supporting member for supporting said frame, and said support rail and said supporting member being at a substantially same height relative to each other.

16. A method for freezing, transporting or storing a biopharmaceutical material, the method comprising:
   providing a supporting structure configured to support a container of biopharmaceutical material;
   providing a connecting structure configured to releasably connect the container of biopharmaceutical material to the supporting structure;
   sealing the container to preserve biopharmaceutical material held therein; and
   locating the supporting structure on a support rail of a transportation cart such that the support rail supports the supporting structure.

17. The method of claim 16 wherein the supporting structure comprises a frame and the locating comprises moving the frame from a cavity of a temperature control unit to a channel of the transportation cart.

18. The method of claim 17 wherein a bottom surface of the cavity and a bottom surface of the channel are located at about a same height relative to each other.

19. The method of claim 17 further comprising moving the frame from the support rail to a support member of the temperature control unit, the support rail and the support member being at about a substantially same height relative to each other.

20. The method of claim 16 further comprising locating an alignment tab of the transportation cart in a recess of a temperature control unit to align the support rail and a support member of a temperature control unit.

21. The method of claim 16 further comprising engaging a fork of a forklift with a forklift slot of the transportation cart and transporting the cart utilizing the forklift.

22. The method of claim 16 further comprising moving the biopharmaceutical material by moving the transportation cart.

23. The method of claim 16 further comprising removing liquid from a drip tray of the transportation cart.

24. A system for transporting and storing a biopharmaceutical material, said system comprising:
   a supporting structure configured to support a container of biopharmaceutical material;
   a connecting structure releasably connecting said container of biopharmaceutical material to said supporting structure;
   said container being sealed to preserve biopharmaceutical material held therein;
   a channel configured to receive said supporting structure and said container or biopharmaceutical material; and
   at least one channel support configured to support said supporting structure and said container in said channel.

* * * * *

UNITED STATES PATENT AND TRADEMARK OFFICE
CERTIFICATE OF CORRECTION

| | | |
|---|---|---|
| PATENT NO. | : 7,104,074 B2 | Page 1 of 1 |
| APPLICATION NO. | : 10/455223 | |
| DATED | : September 12, 2006 | |
| INVENTOR(S) | : Voute et al. | |

It is certified that error appears in the above-identified patent and that said Letters Patent is hereby corrected as shown below:

Claim 8: Column 16, Line 36, delete "wit" and insert --with--

Claim 13: Column 16, Line 54, delete "arid" and insert --and--

Claim 14: Column 16, Line 61, delete "some" and insert --same--

Signed and Sealed this

Ninth Day of January, 2007

JON W. DUDAS
*Director of the United States Patent and Trademark Office*